United States Patent [19]

Lafferty et al.

[11] Patent Number: 4,978,660
[45] Date of Patent: Dec. 18, 1990

[54] α-ADRENERGIC RECEPTOR ANTAGONISTS

[75] Inventors: John J. Lafferty, Levittown; Robert M. DeMarinis, Ardmore; Joseph W. Venslavsky, Wayne, all of Pa.

[73] Assignee: SmithKline Beecham Corporation, Philadelphia, Pa.

[21] Appl. No.: 362,122

[22] Filed: Jun. 6, 1989

Related U.S. Application Data

[63] Continuation-in-part of Ser. No. 200,816, Jun. 1, 1988, abandoned.

[51] Int. Cl.$^5$ .................. A61K 31/55; C07D 491/048
[52] U.S. Cl. ...................... 514/215; 514/81; 540/542; 540/581
[58] Field of Search .................. 540/542, 581; 514/81, 514/215

[56] References Cited

U.S. PATENT DOCUMENTS

| | | | |
|---|---|---|---|
| 3,833,591 | 9/1974 | McManus | 540/471 |
| 3,904,645 | 9/1975 | McManus | 540/84 |
| 3,906,000 | 9/1975 | McManus | 540/547 |
| 4,469,634 | 9/1984 | DeMarinis | 540/594 |

FOREIGN PATENT DOCUMENTS

WO8700522  1/1987  PCT Int'l Appl. ................. 548/450

Primary Examiner—Robert T. Bond
Attorney, Agent, or Firm—Mary E. McCarthy; Stuart R. Suter; Edward T. Lentz

[57] ABSTRACT

α-adrenoceptor antagonists having the formula:

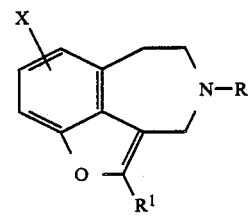

which are useful to produce α-adrenoceptor antagonism, pharmaceutical compositions including these antagonists, and methods of using these antagonists to produce α-adrenoceptor antagonism in mammals.

19 Claims, No Drawings

α-ADRENERGIC RECEPTOR ANTAGONISTS

REFERENCE TO EARLIER APPLICATION

This application is a continuation-in-part of application Ser. No. 07/200,816, filed June 1, 1988, now abandoned.

FIELD OF THE INVENTION

This invention relates to novel 2-substituted-3,4,5,6-tetrahydrofuro[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types α and β. Based upon selectivity of the receptors for a series of agonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, *J. Med. Chem.*, 25, 1389 (1982)). Experiments using 6-chloro-9-(3-methyl-2-butenyloxy)-3-methyl-2,3,4,5-tetrahydro 1H-3-benzazepine (SK&F 104078) demonstrated that the classical adrenoceptors are heterogeneous and can be divided into SK&F 104078—insensitive and SK&F 104078—sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, July 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methyl norepinephrine, and tramazoline which preferentially activate $\alpha_2$ adrenoceptors. Examples of selective α-adrenoceptor antaqonists include prazosin which has high selectivity for $\alpha_1$ adrenoceptors; and the $\alpha_2$-selective blockers yohimbine and rauwolscine.

U.S. Pat. No. 4,469,634, dated Sept. 4, 1984, describes allyloxy and allythio 2,3,4,5-tetrahydro-1H-3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

These compounds are useful as hypoglycemic agents.

PCT Application Number W0 87/00522 describes a series of 4-aminotetrahydrobenz[c,d] indoles and tetrahydroazepino[3,4,5-c,d]indoles having the general formula:

in which A-B is —CH$_2$—CH(NRR)—CH$_2$ or —CH$_2$—CH$_2$—NR—CH$_2$. These compounds are dopamine agonists useful as hypotensives.

SUMMARY OF THE INVENTION

The present invention resides in the discovery that various 2-substituted 3,4,5,6-tetrahydrofuro-[4,3,2-ef][3] benzazepine compounds are α-adrenoceptor antagonists or are useful in preparing α-adrenoceptor antagonists. Presently preferred compounds of the invention include:
ethyl 7-chloro-3,4,5,6-tetrahydro-4-methylfuro[4,3,2-ef][3]benzazepine-2-carboxylate;
7 chloro 3,4,5,6 tetrahydro 4-methylfuro[4,3,2-ef][3]benzazepine 2 methanol;
7-chloro-3,4,5,6-tetrahydro-4-methylfuro[4,3,2-ef][3]benzazepine-2-carboxaldehyde;
methyl 7 chloro-3,4,5,6 tetrahydro-4-methylfuro[4,3,2 ef][3]benzazepine-2-carboxylate;
7-chloro-3,4,5,6-tetrahydro-2,4dimethylfuro[4,3,2-ef][3]benzazepine;
2-bromo-7-chloro 3,4,5,6-tetrahydro 4-methylfuro[4,3,2-ef][3]benzazepine;
2-propenyl 7 chloro-3,4,5,6 tetrahydro-4-methylfuro[4,3,2 ef][3]benzazepine 2-carboxylate;
7-chloro 3,4,5,6-tetrahydro-4-methylfuro[4,3,2-ef][3]benzazepine-2-carbonitrile;
7-chloro-3,4,5,6-tetrahydro-4-methylfuro[4,3,2-ef][3]benzazepine;
7 chloro 2 ethyl 3,4,5,6-tetrahydro 4-methylfuro[4,3,2-ef][3]benzazepine;
ethyl 7-chloro-3,4,5,6-tetrahydro-4-methylfuro[4,3,2-ef][3]benzazepine-2-propanoate; 3, ]benzazepine-2 propanol;
7-chloro-3,4,5,6-tetrahydro-4-methyl-2-(2-propenyloxy)methyl]furo[4,3,2 ef][3]benzazepine;

7-chloro 3,4,5,6 tetrahydro-4-methyl-2-(propyloxy)methyl]furo[4,3,2-ef][3]benzazepine;

7-chloro 3,4,5,6 tetrahydro-4-methyl-2-[(3-methyl-2-butenyloxy)methyl]furo[4,3,2-ef][3]benzazepine;

7 chloro-3,4,5,6-tetrahydro-4-methyl-2-[(2-propenylthio)methyl]furo[4,3,2-ef][3]benzazepine;

7-chloro-3,4,5,6-tetrahydro-4-methyl-2-(trifluoromethyl)furo[4,3,2-ef][3]benzazepine;

7-chloro-3,4,5,6 tetrahydro-4-methylfuro[4,3,2ef][3]benzazepine-2-carboxamide;

N-butyl-7-chloro 3,4,5,6-tetrahydro 4-methylfuro[4,3,2-ef][3]benzazepine-2-carboxamide;

N,N dimethyl-7 chloro 3,4,5,6 tetrahydro 4methylfuro[4,3,2-ef][3]benzazepine 2-carboxamide;

7 chloro-3,4,5,6-tetrahydro-4-methyl-N-(phenylmethyl)furo[4,3,2 ef][3]benzazepine 2-carboxamide;

7-chloro-3,4,5,6 tetrahydro 4-methyl-N-(phenylmethyl)furo[4,3,2-ef][3]benzazepine-2-carboxamide;

7 chloro 3,4,5,6-tetrahydro N-4 -dimethyl-N-(2-phenylethyl)furo[4,3,2-ef][3]benzazepine 2-carboxamide;

7-chloro-3,4,5,6-tetrahydro-4-methyl-N-(3-phenylpropyl)furo[4,3,2-ef][3]benzazepine 2-carboxamide;

phenylmethyl 7-chloro-3,4,5,6 tetrahydro 4-methylfuro[4,3,2-ef][3]benzazepine-2-propanoate;

2,7-dichloro-3,4,5,6-tetrahydro-4-methylfuro[4,3,2-ef][3]benzazepine;

7-chloro-2-[(4-chlorophenyl)methyloxy]-3,4,5,6-tetrahydro-4-methylfuro[4,3,2-ef][3]benzazepine;

7-fluoro-3,4,5,6-tetrahydro-4-methylfuro[4,3,2-ef][3]benzazepine-2-methanol;

7-chloro-9-dimethylamino-3,4,5,6-tetrahydro4-methylfuro[4,3,2-ef][3]benzazepine-2-methanol;

7-bromo-3,4,5,6-tetrahydro-4-methylfuro[4,3,2-ef][3]benzazepine-2-methanol;

7-dimethylamino-3,4,5,6-tetrahydro-4-methylfuro[4,3,2-ef][3]benzazepine-2-methanol;

ethyl 7-cyano-3,4,5,6-tetrahydro-4-methylfuro[4,3,2-ef][3]benzazepine-2-carboxylate;

ethyl 7-chloro-9-dimethylamino-3,4,5,6-tetrahydro-4-methylfuro[4,3,2-ef][3]benzazepine-2carboxylate;

ethyl 7-chloro-9-methylamino-3,4,5,6-tetrahydro-4-methylfuro[4,3,2-ef][3]benzazepine-2Carboxylate;

ethyl 7,9-dichloro-3,4,5,6-tetrahydro-4-methylfuro[4,3,2-ef][3]benzazepine-2-carboxylate; and ethyl 7-dimethylamino-3,4,5,6-tetrahydro-4-methylfuro[4,3,2-ef][3]benzazepine-2-carboxylate.

In a further aspect of the invention there are provided methods of antagonizing α adrenoceptors in mammals, including humans, that comprise administering internally to a subject an effective amount of a 2-substituted-3,4,5,6-tetrahydrofuro[4,3,2-ef][3]benzazepine compound.

Included in the Present invention are pharmaceutical compositions that include compounds useful in the method of the invention and a suitable pharmaceutical carrier. Preferably, these compositions are used to produce α adrenoceptor antagonism and contain an effective amount of compounds useful in the methods of the invention.

DETAILED DESCRIPTION OF THE INVENTION

The presently invented compounds that are α-adrenoceptor antagonists or are useful in preparing α-adrenoceptor antagonists are represented by the following Formula (I):

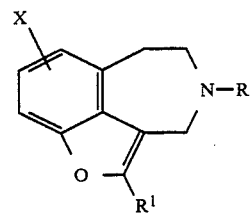

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, , $SC_{1-4}$alkyl, $S(CH_2)_{0-6}$aryl, $SCF_3$, or any accessible combination thereof of up to three substituents;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1-position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$; each $R^{13}$ independently is H or $C_{1-6}$alkyl;

$R^{14}$ and $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I. $CF_3$, or $(CH_2)_{0-6}$aryl;

Y and Z independently are H or $C_{1-6}$alkyl;

$R^2$, $R^3$, and $R^4$ indeperdently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, aryl means a phenyl group which is unsubstituted or substituted by, , $C_{1-6}$alkyl, $C_{1-6}$alkoxy, halo, $CF_3$, or CN, and "any accessible combination thereof" means any combination of up to three substituents on the phenyl moiety that is available by chemical synthesis and is stable.

Formula (Ia) includes presently preferred Formula (I) compounds:

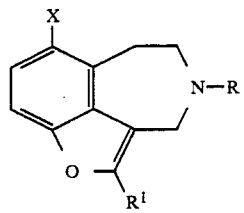

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, or $SCF_3$;

R is H, $C_{1-6}$alkyl, or $C_{3-5}$alkenyl;

$R^1$ is W, $(CH_2)_{0-2}CWYZ$, or $C_{3-5}$alkenyl, except where the double bond is in the 1-position;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$; each $R^{13}$ independently is H or $C_{16}$alkyl;

$R^{14}$ $R^{15}$ independently are $C_{1-6}$alkyl or $(CH_2)_{0-6}$aryl;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}$aryl;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

Compounds of Formula (I) are prepared by the synthetic pathways shown in Schemes I through IV. In Schemes I through IV, W, X, Y, and Z are as defined in Formula (I).

SCHEME I

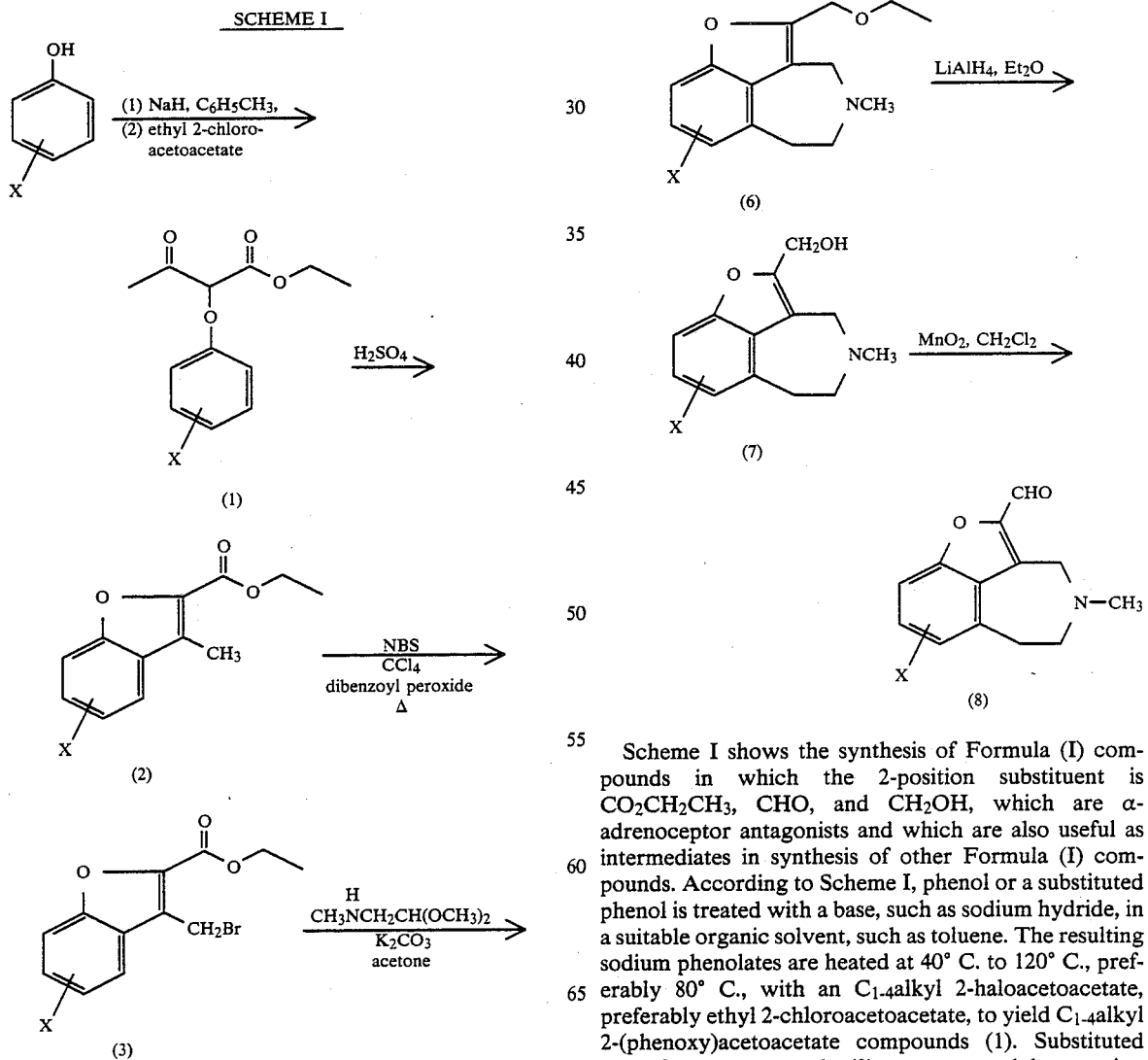

Scheme I shows the synthesis of Formula (I) compounds in which the 2-position substituent is $CO_2CH_2CH_3$, CHO, and $CH_2OH$, which are α-adrenoceptor antagonists and which are also useful as intermediates in synthesis of other Formula (I) compounds. According to Scheme I, phenol or a substituted phenol is treated with a base, such as sodium hydride, in a suitable organic solvent, such as toluene. The resulting sodium phenolates are heated at 40° C. to 120° C., preferably 80° C., with an $C_{1-4}$alkyl 2-haloacetoacetate, preferably ethyl 2-chloroacetoacetate, to yield $C_{1-4}$alkyl 2-(phenoxy)acetoacetate compounds (1). Substituted benzofuran compounds (2) are prepared by treating formula (1) compounds with a strong acid, preferably sulfuric acid, at from −40° C. to 48° C., preferably 0° C.

Formula (2) compounds are treated with a halogenating agent, preferably N bromosuccinimide (NBS), and an initiator, preferably dibenzoylperoxide, in an inert organic solvent, preferably carbon tetrachloride (CCl$_4$), preferably at reflux, to produce formula (3) compounds. Formula (4) compounds are prepared by dissolving formula (3) compounds in an organic solvent, such as acetone, and adding a suitable base, preferably potassium carbonate (K$_2$CO$_3$), and an N-(C$_{1-6}$alkyl)-aminoacetaldehyde di (C$_{1-4}$alkyl) acetal, preferably methylaminoacetaldehyde dimethyl acetal.

Formula (4) compounds are treated with acid, preferably trifluoromethanesulfonic acid in trifluoromethanesulfonic anhydride, to yield enamine compounds of formula (5). Formula (5) compounds are treated with a reducing agent, preferably diborane, in an inert organic solvent, such as tetrahydrofuran, or reduced catalytically to give benzazepine compounds of formula (6).

Thereafter, formula (6) compounds are added to a suitable reducing agent, preferably lithium aluminum hydride (LAH), in an inert solvent, preferably ethyl ether, to yield formula (7) compounds. Formula (7) compounds are treated with a suitable oxidizing agent, preferably manganese dioxide, in an inert solvent, preferably dichloromethane, to give benzazepine-2-carboxaldehyde compounds of formula (8).

Scheme II shows synthesis of Formula (I) compounds in which the 2 position substituent is CH$_2$CWYZ. In Scheme II, X, W, Y and Z are as defined in Formula (I). According to Scheme II, formula (9) compounds are obtained from formula (8) compounds and a phosphonate or a phosphonium salt by treatment with a base, such as sodium hydride, in a suitable solvent, such as ethyl ether. The phosphonates or phosphonium salts are selected so that W and Y are the same as in the desired formula (11) compounds. The metal cation (M$^+$) associated with phosphonate is derived from the base used in this step in the synthesis. Suitable metal ions include lithium, sodium, and potassium.

Formula (9) compounds where W is CHO are prepared by reacting formula (8) compounds with a dialkyl phosphonoacetaldehyde dialkyl acetal, preferably diethyl phosphonoacetaldehyde diethyl acetal, followed by acid hydrolysis.

Formula (10) compounds where W is COR$^2$, CO$_2$R$^5$, SOR$^5$, SO$_2$R$^5$, SO$_3$R$^2$, SO$_2$NR$^3$R$^4$, P(O)OR$^3$(OR$^4$), P(O)R$^5$(OR$^3$), P(O)R$^5$R$^6$, P(O)(OR$^2$)NR$^3$R$^4$, P(O)(NR$^3$R$^4$)$_2$, or P(O)R$^5$(NR$^3$R$^4$) are prepared by reduction of the corresponding formula (9) compounds with hydrogen and a suitable catalyst, preferably platinum oxide, in a suitable solvent, such as ethanol.

Formula (9) compounds where W is CHO are reduced catalytically as the acetal followed by acid hy-

SCHEME II

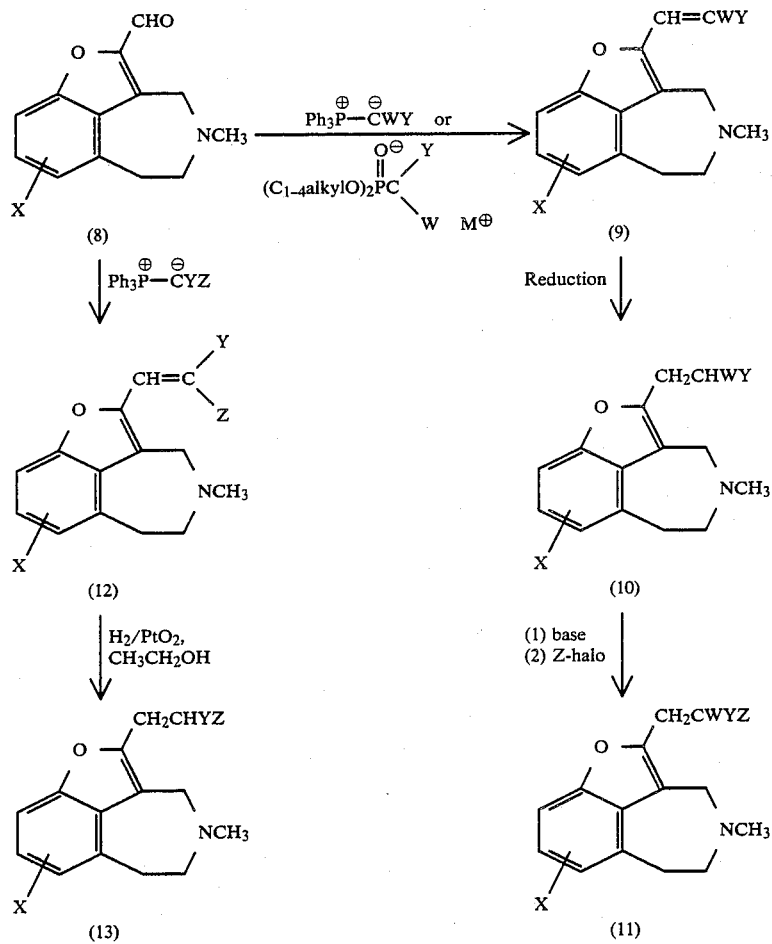

drolysis to produce formula (10) compounds wherein W is CHO.

Formula (9) compounds where W is $NO_2$ or CN are reduced with a metal hydride, such as sodium borohydride, in a suitable solvent preferably isopropanol, to produce formula (10) compounds where W is $NO_2$ or CN.

Formula (10) compounds where W is $CO_2H$ are prepared by hydrolyzing formula (10) compounds where W is $CO_2R^5$ with a strong acid, such as hydrochloric acid in acetic acid. Formula (10) compounds where W is $CONR^3R^4$ are prepared from formula (10) compounds where W is $CO_2H$ by treatment with a known halogenating agent, such as thionyl chloride, followed by reaction with an amine $HNR^3R^4$ or by treatment of a formula (10) compound where W is $CO_2R^5$ with an amine $HNR^3R^4$.

Formula (10) compounds may be converted to formula (11) compounds by treatment with a strong base, such as lithium diisopropylamide, in a suitable inert solvent, preferably tetrahydrofuran, to give an anion which is alkylated with an alkyl halide or an alkyl sulfonate.

Formula (12) compounds are prepared from formula (8) compounds by treatment with an alkyltriphenylphosphonium salt, such as methyltriphenylphosphonium bromide, and a base, such as sodium hydride, in a suitable solvent, such as dimethylformamide and ethyl ether. The phosphonium salts are selected so that Y and Z are the same as in the desired formula (12) compounds. Formula (13) compounds are prepared from formula (12) compounds by reduction with hydrogen and a suitable catalyst, preferably platinum oxide, in a suitable solvent, such as ethanol.

SCHEME III

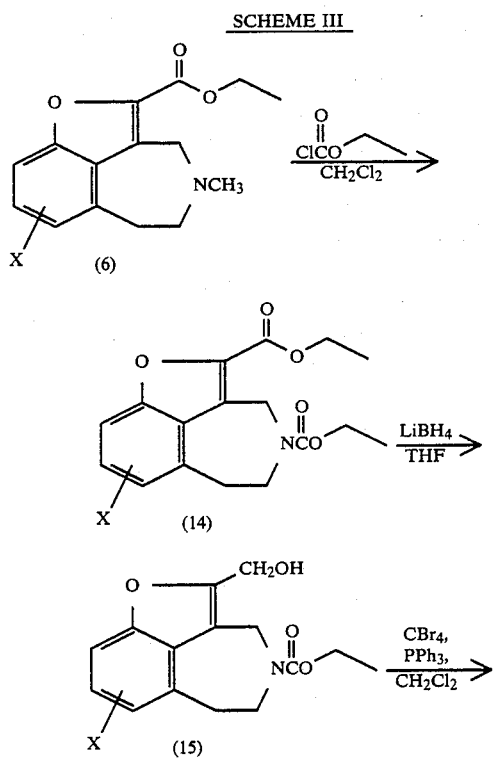

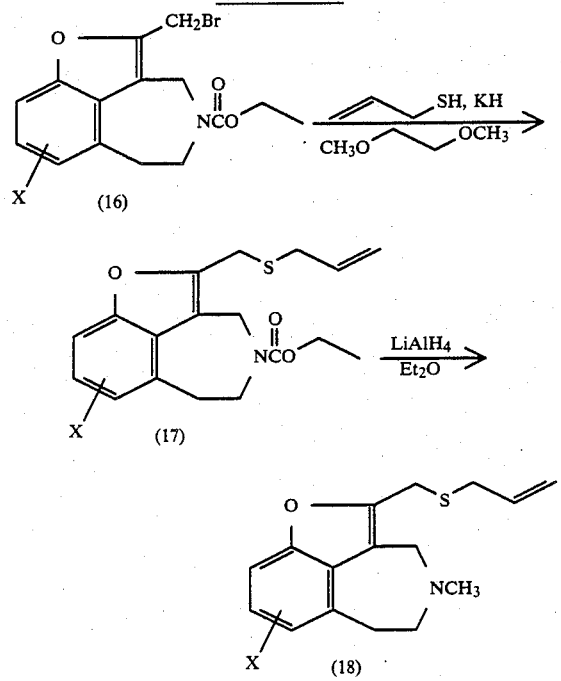

Scheme III shows formation of Formula (I) compounds in which the 2 position substituent is W, $CH_2CWYZ$ and CWYZ. In scheme III, X is as defined in Formula (I). According to Scheme III, formula (14) compounds are prepared from Scheme I, formula (6) compounds by treatment with a suitable haloformate, preferably ethyl chloroformate. Other haloformates, such as trichloroethyl chloroformate also may be employed. Formula (14) compounds are treated with a suitable reducing agent, such as lithium borohydride, in a suitable solvent, preferably tetrahydrofuran, to give formula (15) compounds. Formula (16) compounds are prepared from formula (15) compounds by treatment with a suitable halogenating agent, such as carbon tetrabromide and triphenylphosphine, in a suitable solvent, preferably methylene chloride.

Formula (15) compounds also may be converted to chlorides or sulfonates by treatment with a suitable reagent, such as thionyl chloride or methane sulfonyl chloride, and a suitable base, such as triethylamine, in a suitable solvent, preferably methylene chloride. The halide or sulfonate group in formula (22) compounds may be displaced by a neuclophile, for example, cyanide ion, in a suitable solvent, such as acetonitrile, using a crown ether catalyst, such as 18-crown-6, to give Formula (I) compounds in which the 2-position substituent is CWYZ, where W is CN and Y and Z are each hydrogen atoms. This product may be elaborated further to produce Formula (I) compounds in which the 2-position substituent is CWYZ, where W is CN and Y and Z are each $C_{1-6}$alkyl or Y is a hydrogen atom and Z is a $C_{1-6}$alkyl group. These products may be formed by treatment of the above Formula (I) compounds with a strong base, such as lithium diisopropylamide, in a suitable inert solvent, preferably tetrahydrofuran, to give an anion which is alkylated with an alkyl halide or an alkyl sulfonate to produce the desired Formula (I) compounds.

Formula (I) compounds in which the 2-position substituent is (CH$_2$)$_2$CWYZ are formed in a fashion similar to that described for the preparation of compounds in which the 2-position substituent is CWYZ. In this case, the starting alcohol is a Scheme II, formula (11) compound in which W is CH$_2$OH and Y and Z are each hydrogen atoms. These formula (11) compounds may be converted to chlorides or sulfonates by treatment with a suitable reagent, such as thionyl chloride or methanesulfonyl chloride, and a suitable base, such as triethylamine, in a suitable solvent, preferably methylene chloride. The halide or sulfonate group may be displaced by a nucleophile, for example, cyanide ion, in a suitable solvent, such as acetonitrile, using a crown ether catalyst, such as 18-crown-6, to give Formula (I) compounds in which the 2-position substituent is (CH$_2$)$_2$CWYZ, where W is CN and Y and Z are each hydrogen atoms. The desired Formula (I) compounds in which the 2-position substituent is (CH$_2$)$_2$CWYZ where W is CN and Y and Z are each C$_{1-6}$alkyl or Y is a hydrogen atom and Z is a C$_{1-6}$alkyl group, may be prepared from the above Formula (I) compounds by treatment with a strong base, such as lithium diisopropylamide, in a suitable inert solvent, preferably tetrahydrofuran, to give an anion which is alkylated with an alkyl halide or an alkyl sulfonate.

Formula (I) compounds in which the 2-position substituent is C$_{3-5}$alkenyl, except where the double bond is in the 1-position, may be prepared from Scheme II, formula (11) compounds, where Y and Z are each hydrogen atoms or Y is a hydrogen atom and Z is a C$_{1-6}$alkyl group and w is CH$_2$OH. These formula (11) compounds may be treated with a halogenating agent, such as thionyl chloride, and a suitable base, such as triethylamine, to give the corresponding halides. These compounds may be treated with a strong base, such as lithium diisopropylamide, to give the desired Formula (I) compounds in which the 2-position substituent is C$_{3-5}$alkenyl, except where the double bond is in the 1-position.

Formula (17) compounds are prepared from formula (16) compounds by treatment with an alkyl mercaptan and a suitable base, preferably potassium hydride, in a suitable solvent, such as 1,2 dimethoxyethane.

Formula (18) compounds are prepared from formula (17) compounds by reduction with a suitable reagent, preferably lithium aluminum hydride, in a suitable solvent, such as ethyl ether.

Compounds of formula (16) also may be treated with a variety of known nucleophiles, examples being: nitrogen compounds, such as nitrite; carbon compounds, such as t-butyl lithioacetate; sulfur compounds, such as sodium phenylsulfinate; and phosphorus compounds, such as triethylphosphite; to give Formula (I) compounds.

Scheme I, formula (7) compounds also may be treated with halogenating agents, such as thionyl chloride, to give halo compounds similar to formula (16) compounds where the ethoxycarbonyl group is replaced by a methyl group. Halo compounds obtained from formula (7) compounds may be treated with a variety of nitrogen, carbon, sulfur and phosphorus nucleophiles to give Formula (I) compounds directly.

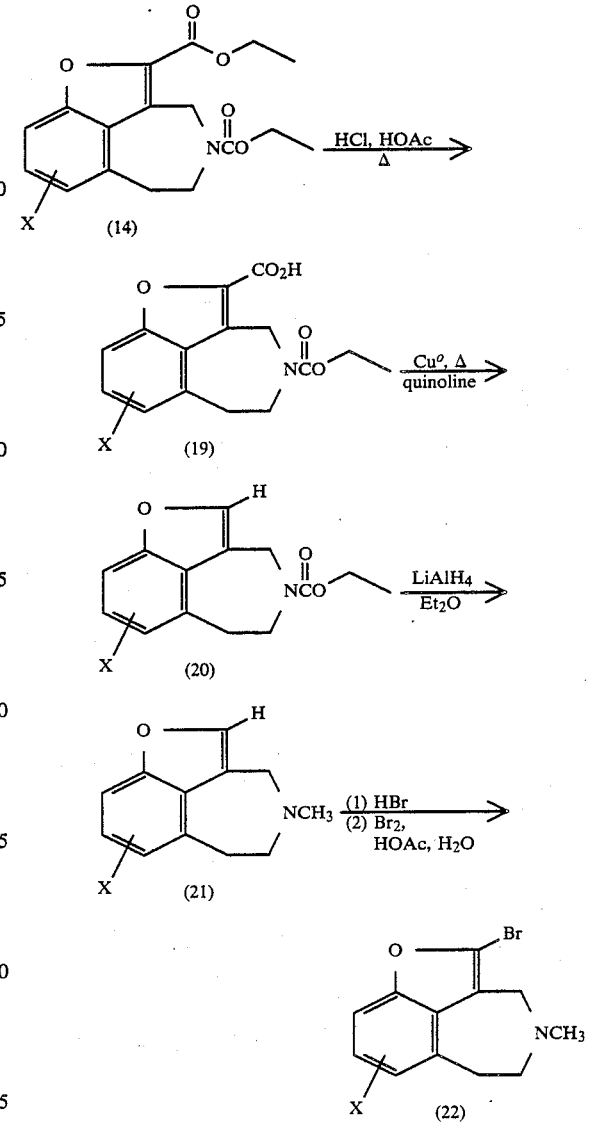

Scheme IV illustrates preparation of Formula (I) compounds in which the 2-position substituent is hydrogen or halo. In Scheme IV, X is as defined in Formula (I). According to Scheme IV, formula (14) compounds are hydrolyzed to formula (19) compounds with strong acid, preferably hydrochloric acid in acetic acid. Formula (19) compounds are decarboxylated, preferably by treatment with copper powder and quinoline, at a temperature of 150° to 250° C., preferably 200° C., to give formula (20) compounds. Formula (20) compounds are reduced with a suitable reagent, preferably lithium aluminum hydride, in a suitable solvent, such as ethyl ether, to yield formula (21) compounds. Formula (21) compounds are converted to hydrobromides and treated with a suitable brominating agent, preferably bromine, in a suitable solvent, such as aqueous acetic acid, to yield formula (22) compounds.

Formula (I) compounds in which the 2-position substituent is chloro are prepared in a similar way by treating formula (21) compounds as their hydrochlorides with chlorine.

Formula (I) compounds in which the 2-position substituent is phenyl or a $SR^5$ group are prepared from formula (21) compounds by treatment with a lithiating agent, such as butyl lithium, in a suitable solvent, such as tetrahydrofuran, to form the corresponding 2-lithio derivative. This intermediate is treated with a $(R^5)_2$disulfide species, wherein $R^5$ is as defined in formula (I) compounds, to form the 2-$SR^5$ compounds. Alternately, the 2-lithio intermediate is treated with a tri-alkyltin halide, such as tributyltin chloride, followed by reaction with an aryl halide, such as iodobenzene, in the presence of a palladium catalyst such as bis(triphenylphosphine)palladium (II) chloride, to produce Formula (I) compounds wherein the 2-position substituent is phenyl.

Schemes I through IV outline preparation of Formula (I) compounds in which R is methyl. Formula (I) compounds wherein R is other than methyl are formed by selecting the N ($C_{1-6}$alkyl)aminoacetaldehyde di($C_{1-4}$alkyl) acetal used in preparing the formula (4) compounds of Scheme I so that the nitrogen is desirably substituted. Alternatively, Formula (I) compounds wherein R is other than methyl are prepared by reacting a Formula (I) compound wherein R is material with an alkyl haloformate, preferably trichloroethyl chloroformate, at approximately 50° C. to 100° C. to produce a trihaloalkyl carbamate. To this carbamate dissolved in a suitable organic solvent, such as tetrahydrofuran, is added an acid, preferably acetic acid, and a reducing agent, such as zinc dust, to yield a product in which R is hydrogen. This subsequently is reacted with a halo-$R^7$ compound, wherein $R^7$ is $C_{2-6}$alkyl or $C_{3-5}$alkenyl, to yield Formula (I) compounds wherein R is $C_{2-6}$alkyl or $C_{3-5}$alkenyl, respectively.

The substituted phenols and $C_{1-4}$alkyl 2-haloacetoacetates used as starting materials in Scheme I are commercially available or can be synthesized from available materials by known methods. Additionally, the reactants used in Schemes I through IV are available or can be synthesized from available materials by known methods.

The pharmaceutically acceptable, nontoxic, acid addition salts having the utility of the free bases of Formula (I), are formed with inorganic or organic acids, by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are $\alpha$-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The $\alpha$-adrenoceptor activity of certain compounds of the present invention was determined using the following in vitro systems.

Alpha$_1$ adrenoceptor antagonist activity was determined using the rabbit aorta. Male New Zealand White rabbits (2-4 Kg) were euthanized by cervical concussion. A 4 cm portion of the thoracic aorta was removed and placed in a dish of cold (10° C.) Krebs Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 $\mu$M) to block neuronal uptake and propranolol (1 $\mu$M) to block beta-adrenoceptors. Tissues were usually challenged once with norepinephrine (0.1 $\mu$M) during the equilibration period to check for viability.

A cumulative concentration-response curve to norepinephrine was obtained in each aortic segment. Following washout of norepinephrine, the $\alpha$ adrenoceptor antagonist to be tested was added to the bath. After the tissue had been in contact with the antagonist for 30-60 minutes, the norepinephrine concentration response curve was repeated in the presence of antagonist. The tissue was then washed again, and a tenfold higher concentration of antagonist added. Following equilibration (30-60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283-335 (Springer 1972)). The $K_B$ value obtained at each antagonist concentration was averaged to obtain a mean $K_B$ for each experiment.

Alpha$_2$ adrenoceptor antagonist activity of the compounds was determined using the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known $\alpha_2$ agonist) is prepared by administering increasing concentrations of B-HT 920 following each successive stimulation. The tissue then is superfused for thirty minutes with the $\alpha$-adrenoceptor antagonist to be tested and the B-HT 920 concentration effect curve is repeated in the presence of antagonist. Data are reported as $K_B$, defined above. Additional details of this test system are found in Hieble, J. P. and R. G. Pendleton, *Arch. Pharmacol.*, 309:217-224 (1979).

Alpha₃ adrenoceptor antagonist receptor activity was determined using the dog saphenous vein (DSV) as the test system. This test system has been shown a suitable preparation in which to characterize postsynaptic $\alpha_2$ ($\alpha_3$) adrenoceptors, Sullivan, A. T. and G. M. Drew, *Arch. Pharmacol.*, 314:249-258 (1980). This test system is prepared by removing the lateral saphenous vein from an anesthetized dog and cutting the vein into segments of 4 mm in length. Segments are mounted as described for the isolated rabbit aorta.

The $\alpha_3$ adrenoceptor antagonist activity of the compounds of interest is determined by measuring shifts in the dose response curve of a specific agonist induced by the tested compounds. The $\alpha_2$, $\alpha_3$ agonist, B-HT 920, was used in testing the compounds listed in Table I.

Representative Formula (I) compounds which were tested using the above described in vitro test systems are listed in Table 1. Each of the compounds tested was found to have antagonist activity at one or more of the $\alpha$-adrenoceptor subtypes.

Table 1 ethyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-methanol;
7-chloro-3,4,5,6-tetrahydro-4-methylfuro[4,3,2-ef][3]benzazepine-2-carboxaldehyde;
methyl 7-chloro-3,4,5,6-tetrahydro-4methylfuro[4,3,2-ef][3]benzazepine-2-carboxylate;
2-propenyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-carbonitrile;
7-chloro-3,4,5,6-tetrahydro-4-methylfuro[4,3,2-ef][3]benzazepine;
7-chloro-2-ethyl-3,4,5,6-tetrahydro-4-methylfuro[4,3,2-ef][3]benzazepine;
ethyl 7-chloro-3,4,5,6-tetrahydro-4-methylfuro[4,3,2-ef][3]benzazepine-2-propanoate;
7-chloro-3,4,5,6-tetrahydro-4-methylfuro[4,3,2-ef][3]benzazepine-2-propanol;
7-chloro-3,4,5,6-tetrahydro-4-methyl-2-[(2-propenyloxy)methyl]furo[4,3,2-ef][3]benzazepine;
7-chloro-3,4,5,6-tetrahydro-4-methyl-2[(propyloxy)methyl]furo[4,3,2-ef][3]benzazepine;
7-chloro-3,4,5,6-tetrahydro-4-methyl-2-[(3-methyl-2-butenyloxy)methyl]furo[4,3,2-ef][3]benzazepine;
7-chloro-3,4,5,6-tetrahydro-4-methyl-2-[(2-propenylthio)methyl]furo[4,3,2-ef][3]benzazepine;
7-chloro-3,4,5,6-tetrahydro-4-methyl-2-(trifluoromethyl)furo[4,3,2-ef][3]benzazepine;
7-chloro-3,4,5,6-tetrahydro-4-methylfuro[4,3,2-ef][3]benzazepine-2-carboxamide;
N-butyl-7-chloro-3,4,5,6-tetrahydro-4-methylfuro[4,3,2-ef][3]benzazepine-2-carboxamide;
N,N-dimethyl-7-chloro-3,4,5,6-tetrahydro-4-methylfuro[4,3,2-ef][3]benzazepine-2-carboxamide;
7-chloro-3,4,5,6-tetrahydro-4-methyl-N-(phenylmethyl)furo[4,3,2-ef][3]benzazepine-2-carboxamide;
7-chloro-3,4,5,6-tetrahydro-4-methyl-N-2-phenylethyl)furo[4,3,2-ef][3]benzazepine-2-carboxamide;
7-chloro-3,4,5,6-tetrahydro-N-4-dimethyl-N-(2-phenylethyl)furo[4,3,2-ef][3]benzazepine-2-carboxamide;
7-chloro-3,4,5,6-tetrahydro-4-methyl-N-(3-phenylpropyl)furo[4,3,2-ef][3]benzazepine-2-carboxamide;
phenylmethyl 7-chloro-3,4,5,6-tetrahydro-4-methylfuro[4,3,2-ef][3]benzazepine-2-propanoate;
2,7-dichloro-3,4,5,6-tetrahydro-4-methylfuro[4,3,2-ef][3]benzazepine;
7-chloro-2-[(4-chlorophenyl)methyloxy]-3,4,5,6-tetrahydro-4-methylfuro[4,3,2-ef][3]benzazepine;
7-fluoro-3,4,5,6-tetrahydro-4-methylfuro[4,3,2-ef][3]benzazepine-2-methanol;
7-chloro-9-dimethylamino-3,4,5,6-tetrahydro-4-methylfuro[4,3,2-ef][3]benzazepine-2-methanol;
7-bromo-3,4,5,6-tetrahydro-4-methylfuro[4,3,2-ef][3]benzazepine-2-methanol;
7-dimethylamino-3,4,5,6-tetrahydro-4-methylfuro[4,3,2-ef][3]benzazepine-2-methanol;
ethyl 7 cyano-3,4,5,6-tetrahydro-4-methylfuro[4,3,2-ef][3]benzazepine-2-carboxylate;
ethyl 7-chloro-9-dimethylamino-3,4,5,6-tetrahydro-4-methylfuro[4,3,2-ef][3]benzazepine-2-carboxylate;
ethyl 7-chloro-9-methylamino-3,4,5,6-tetrahydro-4-methylfuro[4,3,2-ef][3]benzazepine-2-carboxylate;
ethyl 7,9-dichloro-3,4,5,6-tetrahydro-4-methylfuro[4,3,2-ef][3]benzazepine-2-carboxylate;
ethyl 7-dimethylamino-3,4,5,6-tetrahydro-4-methylfuro[4,3,2-ef][3]benzazepine-2-carboxylate;
7-chloro-3,4,5,6-tetrahydro-2,4-dimethylfuro[4,3,2-ef][3]benzazepine; or
2-bromo-7-chloro-3,4,5,6-tetrahydro-4-methylfuro[4,3,2-ef][3]benzazepine.

The antihypertensive activity of certain compounds of the present invention was determined using the spontaneously hypertensive rat model. The details of this in vivo test are found in Roesler, J. M., et al.. *J. Pharmacol. Exp. Ther.*, 236:1-7 (1986).

When the compound of Example 25 is tested in spontaneously hypertensive rats following oral administration at 10 mg/kg, no reduction in arterial blood pressure is observed. Higher dose levels and other routes of administration will be tried.

Novel pharmaceutical compositions are obtained when the compounds are incorporated with pharmaceutical carriers into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in pharmaceutical dosage units will be an efficacious, nontoxic quantity selected from the range of 0.01-100 mg/kg of active compound, preferably 0.1-50 mg/kg. The selected dose is administered to a human patient in need of treatment from 1-6 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Ethyl 7-Chloro-3,4,5,6-tetrahydro-4-methylfuro[4,3,2-ef][3]benzazepine-2-carboxylate (i) Ethyl 2-(4-Chlorophenoxy)acetoacetate A 60% dispersion of sodium hydride in mineral oil (40 g, 1 mol) was washed with dry petroleum ether and suspended in dry toluene (700 ml). The suspension was stirred under argon and carefully treated with a solution of 4-chlorophenol (128.6 g, 1 mol) in dry toluene (300 ml) added dropwise. The resulting suspension was stirred for 1 hour, warmed to 80° C. and treated with ethyl 2-chloroacetoacetate (165 g, 1 mol) added dropwise to maintain the internal temperature between 80°-85° C. The resulting solution was stirred at 80° C. for 4 hours, cooled and carefully treated with ice. The organic phase was washed with water (3×200 ml), 10% sodium hydroxide (2×75 ml), water (20 ml) and brine (100 ml), dried with magnesium sulfate, filtered and concentrated. The resulting oil was distilled in vacuo [bp 126°-132° C. (0.1 mm)] to give 95 g (37%) of ethyl 2-(4-chlorophenoxy) acetoacetate.

(ii) Ethyl 5-Chloro-3-methyl-2-benzofurancarboxylate

Ethyl 2 (4-chlorophenoxy)acetoacetate (90.3 g, 0.353 mol) was added dropwise to sulfuric acid (240 ml) stirred at 0° C. The resulting suspension was stirred at 0° C. for 3.5 hours, poured onto crushed ice and the mixture stirred for 0.5 hours. The mixture was extracted with toluene and the organic phase was washed with 5% sodium bicarbonate and water. The organic phase was dried with magnesium sulfate, filtered and concentrated. The crude product was recrystallized from cyclohexane to give 54.5 g (65%) of ethyl 5-chloro-3-methyl-2-benzofuran carboxylate: mp 80°-82° C.

(iii) Ethyl 3-Bromomethyl-5-chloro-2-benzofurancarboxylate

A mixture of ethyl 5-chloro-3-methyl-2-benzofurancarboxylate (52.5 g, 0.22 mol), N bromosuccinimide (39.15 g, 0.22 mol) and benzoyl peroxide (0.4 g) in carbon tetrachloride (750 ml) was stirred and refluxed for 10 hours. The mixture was cooled, filtered and the filtrate was concentrated. The crude product was recrystallized from hexane to give 52.8 g (76%) of ethyl 3-bromomethyl-5-chloro-2-benzofurancarboxylate: mp 112°-114° C.

(iv) Ethyl 5-Chloro-3-[N-(2,2-dimethoxyethyl)-N-methyl(aminomethyl)]-2-benzofurancarboxylate A mixture of ethyl 3-bromomethyl-5-chloro-2-benzofurancarboxylate (52.75 g, 0.166 mol), methylaminoacetaldehyde dimethyl acetal (19.0 g, 0.167 mol) and potassium carbonate (45 g) in dry acetone (600 ml) was stirred under argon for 30 hours, filtered and the filtrate evaporated. The residue was partitioned between ethyl ether and water and the organic phase was dried with magnesium sulfate, filtered, and concentrated to give ethyl 5-chloro-3-[N-(2,2-dimethoxyethyl)-N-methyl(aminomethyl)]-2-benzofurancarboxylate: mp 58°-60° C.

(v) Ethyl 7-Chloro-3,4-dihydro-4-methylfuro[4,3,2-ef][3]benzazepine-2-carboxylate Ethyl 5-chloro-3-[N-(2,2-dimethoxyethyl)N-methyl-(aminomethyl)]-2-benzofurancarboxylate (8.5 g, 24 mmol) was added to a mixture of trifluoromethanesulfonic anhydride (3 ml) and trifluoromethanesulfonic acid (30 ml), stirred under argon in a water bath, dropwise over 10 minutes to maintain the internal temperature between 25°-30° C. The mixture was stirred for 0.5 hours, poured into a stirred mixture of ethyl ether (750 ml) and ice water (200 ml) and the aqueous phase was carefully basified with potassium carbonate to pH 9.5. The phases were separated and the aqueous phase was extracted with ethyl ether (2×200 ml). The organic phases were combined, dried with magnesium sulfate, filtered and concentrated to give ethyl 7-chloro-3,4-dihydro-4-methylfuro[4,3,2-ef][3]benzazepine-2-carboxylate.

(vi) Ethyl 7-Chloro-3,4,5,6-tetrahydro-4-methyl-furo[4,3,2-ef][3]benzazepine-2-carboxylate A solution of ethyl 7-chloro-3,4-dihydro-4-methyl-furo[4,3,2-ef][3]benzazepine-2-carboxylate in dry tetrahydrofuran (50 ml) was added to borane in tetrahydrofuran (1 M, 100 ml, 0.1 mol) and stirred under argon at 0° C. The resulting solution was refluxed for 3.5 hours, cooled, carefully treated with ethanol and evaporated. The residue was refluxed in absolute ethanol (125 ml) for 1.5 hours and concentrated. The residual oil was stirred with ethyl ether (500 ml) and the mixture was filtered. The filtrate was treated with hydrogen chloride and the resulting solid was recrystallized from ethanol to give ethyl 7-chloro-3,4,5,6-tetrahydro-4-methylfuro-[4,3,2-ef][3]benzazepine-2-carboxylate hydrochloride: mp 244°-247° C.

EXAMPLE 2

7-Chloro-3,4,5,6-tetrahydro-4-methylfuro-[4,3,2-ef][3]benzazepine-2-methanol A solution of ethyl 7-chloro-3,4,5,6-tetrahydro-4-methylfuro[4,3,2-ef][3]benzazepine-2-carboxylate (5.1 g, 17.4 mmol), prepared as in Example 1, in ethyl ether (100 ml) was added dropwise to a suspension of lithium aluminum hydride (0.85 g, 23 mmol) in ethyl ether (200 ml) and stirred at 0° C. The mixture was refluxed for 2 hours, cooled and treated carefully with water (0.9 ml), 15% sodium hydroxide (0.9 ml) and water (2.7 ml). The resulting suspension was stirred for 15 minutes, filtered and the solvent evaporated to give 2.5 g (57%) of 7-chloro-3,4,5,6-tetrahydro-4-methylfuro[4,3,2-ef][3]benzazepine 2-methanol: mp 124°-128° C. The free base was dissolved in ethyl ether and treated with hydrogen chloride to give 7-chloro-3,4,5,6-tetrahydro-4-methyl-furo-[4,3,2-ef][3]benzazepine-2-methanol hydrochloride: mp 220°-223° C.

EXAMPLE 3

7-Chloro-3,4,5,6-tetrahydro-4-methylfuro[4,3,2-ef][3]benzazepine-2-carboxaldehyde A solution of 7-chloro-3,4,5,6-tetrahydro-4-methyl-furo[4,3,2-ef][3]benzazepine-2-methanol, prepared as in Example 2, (2.5 g, 10 mmol) in dichloromethane (100 ml) was stirred under argon with activated manganese dioxide (25 g) for 2 hours. The mixture was filtered, the filter cake washed with dichloromethane and the filtrate was concentrated to give 2.2 g (88%) of 7-chloro-3,4,5,6-tetrahydro-4-methylfuro[4,3,2-ef][3]benzazepine-2-carboxaldehyde: mp 100°-102° C. The free base

EXAMPLE 4

7-Chloro-3,4,5,6-tetrahydro-4-methylfuro[4,3,2-ef][3]benzazepine-2-carboxylic Acid A suspension of ethyl 7-chloro-3,4,5,6-tetrahydro-4-methylfuro[4,3,2-ef][3]benzazepine-2-carboxylate, prepared as in Example 1, (1 g, 3 mmol) in 6 N hydrochloric acid (10 ml) and acetic acid (10 ml) was heated to reflux for 6 hours, cooled and filtered to give 0.64 g (71%) of 7-chloro-3,4,5,6-tetrahydro-4-methylfuro[4,3,2-ef][3]benzazepine-2-carboxylic acid hydrochloride: mp>260° C. (dec).

EXAMPLE 5

Methyl 7-Chloro-3.4.5.6-tetrahydro-4-methylfuro[4,3,2-ef][3]benzazepine-2-carboxylate A solution of sodium methoxide, prepared from sodium (43 mg, 1.9 mmol) and methanol (5 ml), was treated with a solution of ethyl 7-chloro-3,4,5,6-tetrahydro-4-methylfuro[4,3,2-ef][3]benzazepine-2-carboxylate, prepared as in Example 1, (0.5 g, 1.7 mmol) in methanol (5 ml). The mixture was heated to reflux for 3 hours, cooled, concentrated and the residue partitioned between water and methylene chloride. The organic phase was dried with sodium sulfate, concentrated, dissolved in methanol and treated with hydrogen chloride. The crude hydrochloride salt was recrystallized initially from methanol-ethyl ether and then from ethanol to give 0.16 g of methyl 7-chloro-3,4,5,6-tetrahydro-4-methylfuro[4,3,2-ef][3]-benzazepine-2-carboxylate hydrochloride: mp 223°–224° C. (dec).

EXAMPLE 6 t-Butyl 7-Chloro-3,4,5,6-tetrahydro-4-methylfuro[4,3,2-ef][3]benzazepine-2-carboxylate A mixture of ethyl 7-chloro-3,4,5,6-tetrahydro-4-methylfuro[4,3,2-ef][3]benzazepine-2-carboxylate, prepared as in Example 1, (3.9 g, 13.3 mmol), 5A molecular sieves (50 g), t-butanol (21 ml) and dry toluene (250 ml) was treated with potassium t-butoxide (0.5 g) and stirred at 80° C. for 4 hours. Additional potassium t-butoxide (0.2 g) was added and after 2 hours the mixture was filtered, the filtrate concentrated and the residue partitioned between water and ethyl ether. The organic phase was washed, dried and concentrated to give a crystalline solid which was triturated with petroleum ether to give 1.7 g (40%) of t-butyl 7-chloro-3,4,5,6-tetrahydro-4-methylfuro[4,3,2-ef][3]benzazepine-2-carboxylate: 83°–86° C.

EXAMPLE 7

7-Chloro-3,4,5,6-tetrahydro-4-methylfuro[4,3,2-ef][3]-benzazepine-2-carbonyl Chloride and 2-Propenyl 7-Chloro-3,4,5,6-tetrahydro-4-methylfuro[4,3,2-ef][3]benzazepine-2-carboxylate A mixture of 7-chloro 3,4,5,6-tetrahydro-4-methylfuro[4,3,2-ef][3]benzazepine-2-carboxylic acid hydrochloride, prepared as in Example 4, (0.3 g, 1 mmol) and thionyl chloride (30 ml) was stirred and heated to reflux for 3 hours. The mixture was concentrated and the residue was triturated with hexane. The residue was treated with chloroform, concentrated, treated with toluene and concentrated to give 0.24 g of 7-chloro-3,4,5,6-tetrahydro-4-methylfuro[4,3,2-ef][3]benzazepine-2-carbonyl chloride hydrochloride.

A suspension of 7-chloro-3,4,5,6-tetrahydro-4-methylfuro[4,3,2-ef][3]benzazepine-2-carbonyl chloride hydrochloride (0.22 g, 0.7 mmol) in tetrahydrofuran (10 ml) was stirred and treated with allyl alcohol (0.2 ml, 1.5 mmol) and triethylamine (0.2 ml, 1.4 mmol). The mixture was stirred for 4 hours, poured into ice and extracted with chloroform. The organic phase was washed with water, dried with sodium sulfate, filtered and concentrated. The residue was chromatographed on silica gel eluted with ethyl acetate-hexane (60:40). Fractions containing the product were combined, treated with ethereal hydrogen chloride and concentrated. The crude hydrochloride salt was recrystallized from methanol to give 2-propenyl 7-chloro-3,4,5,6-tetrahydro-4-methylfuro[4,3,2-ef][3]benzazepine-2-carboxylate hydrochloride: mp 212.5°–214.5° C.

EXAMPLE 8

7-Chloro-3,4,5,6-tetrahydro-N,N,4-trimethylfuro[4,3,2-ef][3]benzazepine-2-carboxamide Dimethylamine was bubbled through a suspension of 7-chloro-3,4,5,6-tetrahydro-4-methylfuro[4,3,2-ef][3]benzazepine-2-carbonyl chloride hydrochloride, prepared as in Example 7, (0.2 g) in methylene chloride (30 ml) stirred at 0° C. for 5 minutes. The mixture was stirred for 1 hour, extracted with 10% aqueous sodium hydroxide and water, dried with magnesium sulfate and concentrated in vacuo to give 7-chloro 3,4,5,6-tetrahydro N,N,4-trimethylfuro[4,3,2-ef][3]benzazepine-2-carboxamide.

EXAMPLE 9

7-Chloro-3,4,5,6-tetrahydro-4-methylfuro[4,3,2-ef][3]benzazepine-2-carboxaldehyde Oxime and 7-Chloro-3,4,5,6-tetrahydro-4-methylfuro[4,3,2-ef][3]benzazepine-2-carbonitrile 7-Chloro-3,4,5,6-tetrahydro-4-methylfuro[4,3,2-ef][3]benzazepine-2-carboxaldehyde, prepared as in Example 3, (0.65 g, 2.6 mmol) was added to a solution of hydroxylamine hydrochloride (0.36 g, 5.2 mmol) in ethanol (25 ml) and stirred for 30 minutes. The mixture was filtered to give 7-chloro-3,4,5,6-tetrahydro-4-methylfuro(4,3,2-ef][3]benzazepine-2-carboxaldehyde oxime hydrochloride.

A mixture of 7-chloro-3,4,5,6-tetrahydro-4-methylfuro[4,3,2-ef][3]benzazepine-2-carboxaldehyde oxime hydrochloride and triethylamine (0.82 g, 8.1 mmol) in methylene chloride (50 ml) was stirred and cooled to −78° C. and treated with a solution of trifluoromethanesulfonic anhydride (0.73 g, 2.6 mmol) in methylene chloride (5 ml) added over 10 minutes. The mixture was allowed to warm to 25° C. over 2 hours and was washed with water (3×10 ml) and brine (10 ml), dried and concentrated. The residue was chromatographed on silica gel eluted with ethyl ether. Fractions containing the product were pooled and treated with etheral hydrogen chloride to give 0.25 g (34%) of 7-chloro-3,4,5,6-tetrahydro-4-methylfuro[4,3,2-ef][3]benzazepine 2-carbonitrile hydrochloride: mp>275° C. (dec).

EXAMPLE 10

2-Acetyl-7-chloro-3,4,5,6-tetrahydro-4-methylfuro[4,3,2-ef][3]benzazepine

7-Chloro-3,4,5,6-tetrahydro-4-methylfuro[4,3,2-ef][3]benzazepine-2-carbonitrile, prepared as in Example 9, is treated with methylmagnesium bromide in tetrahydrofuran to give 2-acetyl-7-chloro-3,4,5,6-tetrahydro-4-methylfuro[4,3,2-ef][3]benzazepine.

EXAMPLE 11

7-Chloro-3,4,5,6-tetrahydro-4-methylfuro[4,3,2-ef][3]benzazepine

A solution of t-butyl 7-chloro-3,4,5,6-tetrahydro-4-methylfuro[4,3,2-ef][3]benzazepine-2-carboxylate, prepared as in Example 6, (0.8 g, 2.5 mmol) in methylene chloride (25 ml) was treated with ethyl chloroformate (1.2 g, 11 mmol) and heated to reflux under argon for 24 hours. The mixture was concentrated, treated with methylene chloride and concentrated. The residue was dissolved in ethyl ether, filtered and the filtrate concentrated to give 0.5 g (52%) of t-butyl 7-chloro-4-ethoxycarbonyl-3,4,5,6-tetrahydrofuro[4,3,2-ef][3]benzazepine-2-carboxylate: mP 122°–124° C.

t-Butyl 7-chloro-4-ethoxycarbonyl-3,4,5,6-tetrahydrofuro[4,3,2-ef][3]benzazepine-2-carboxylate (0.5 g, 1.3 mmol) was dissolved in trifluoracetic acid (15 ml) at 0° C. under argon and stirred for 1 hour. The mixture was treated with ice and the resulting solid was filtered, washed and air dried to give 0.35 g (83%) of 7-chloro-4-ethoxycarbonyl-3,4,5,6-tetrahydrofuro[4,3,2-ef][3]benzazepine-2-carboxylic acid: mp 250°–255° C.

A mixture of 7-chloro-4-ethoxycarbonyl-3,4,5,6-tetrahydrofuro[4,3,2-ef][3]benzazepine-2-carboxylic acid (0.35 g, 1.1 mmol) and activated copper powder (1 g) in quinoline (5 ml) was heated to 200° C. for 30 minutes under argon. The mixture was cooled, diluted with ethyl ether, filtered and the filtrated washed with dilute hydrochloric acid, aqueous sodium bicarbonate and water. The filtrated was dried and concentrated to give 0.3 g (100%) of 7-chloro-4-ethoxycarbonyl-3,4,5,6-tetrahydro[4,3,2-ef][3]benzazepine.

A solution of 7-chloro-4-ethoxycarbonyl-3,4,5,6-tetrahydrofuro[4,3,2-ef][3]benzazepine (0.3 g, 1.1 mmol) in ethyl ether (15 ml) was treated with lithium aluminum hydride (60 mg) and stirred for 16 hours. The mixture was cooled and treated sequentially with water (0.07 ml), 15% aqueous sodium hydroxide (0.07 ml) and water (0.21 ml). The mixture was diluted with ethyl ether, stirred and filtered. The filtrate was concentrated and treated with hydrogen chloride to give 95 mg (35%) of 7-chloro-3,4,5,6-tetrahydro-4-methylfuro[4,3,2-ef][3]benzazepine hydrochloride: mp >260° C.

EXAMPLE 12

7-Chloro-3,4,5,6-tetrahydro-2,4-dimethylfuro-[4,3,2-ef][3]benzazepine

A mixture of 7-chloro-3,4,5,6-tetrahydro-4-methylfuro[4,3,2-ef][3]benzazepine-2-methanol hydrochloride, prepared as in Example 2, and platinum oxide (0.16 g) in absolute ethanol (100 ml) was shaken under hydrogen (3 psi) for 1 hour. The mixture was filtered, concentrated, converted to the free base and chromatographed on silica gel eluted with ethyl ether. Fractions containing the product were pooled and treated with hydrogen chloride to give 0.21 g (33%) of 7-chloro-3,4,5,6-tetrahydro-2,4-dimethylfuro[4,3,2-ef][3]benzazepine hydrochloride: mp >260° C.

EXAMPLE 13

7-Chloro-2-ethyl-3,4,5,6-tetrahydro-4-methylfuro[4,3,2-ef][3]benzazepine

A 60% dispersion of sodium hydride in mineral oil (1.0 g, 25 mmol) was washed with dry petroleum ether and suspended in dry dimethylformamide (50 ml) and ethyl ether (50 ml). The suspension was stirred under argon and treated with methyltriphenylphosphonium bromide (10.7 g, 30 mmol). The reaction was stirred for 45 minutes and a solution of 7-chloro-3,4,5,6-tetrahydro-4-methylfuro-[4,3,2-ef][3]benzazepine-2-carboxaldehyde, prepared as in Example 3, (4.5 g, 18 mmol) in dimethylformamide (40 ml) was added over 10 minutes. The reaction was stirred for 1 hour, poured into ice water and extracted with ethyl ether. The combined organic phases were dried with magnesium sulfate and concentrated. The residual solid was dissolved in hexane (200 ml) and cooled to −20° C. The supernatant was decanted, concentrated and treated with ethereal hydrogen chloride. The crude product was recrystallized from acetone to give 1.5 g (30%) of 7-chloro-2-ethenyl-3,4,5,6-tetrahydro-4-methylfuro[4,3,2-ef][3]benzazepine hydrochloride: mp >250° C. (dec).

Using the general procedure of Example 12, replacing 7-chloro-3,4,5,6-tetrahydro-4-methylfuro[4,3,2-ef][3]benzazepine-2-methanol hydrochloride with 7-chloro-2-ethenyl-3,4,5,6-tetrahydro-4-methylfuro[4,3,2-ef][3]benzazepine hydrochloride gave, after recrystallization from acetone, 0.16 g (57%) of 7-chloro-2-ethyl-3,4,5,6-tetrahydro-4-methylfuro[4,3,2-ef][3]benzazepine hydrochloride: mp 234° C.

EXAMPLE 14

7-Chloro-3,4,5,6-tetrahydro-4-methyl-2-(2-methylpropyl)furo[4,3,2-ef][3]benzazepine A solution of butyllithium in hexane (2.6 M, 1.3 ml, 3.4 mmol) was added to a suspension of isopropyltriphenylphosphonium iodide (1.5 g, 3.4 mmol) in freshly distilled tetrahydrofuran (20 ml) stirred under argon at −15° C. The mixture was stirred at −10° C. to −15° C. for 20 minutes and treated with a solution of 7-chloro-3,4,5,6-tetrahydro-4-methylfuro[4,3,2-ef][3]benzazepine-2-carboxaldehyde, prepared as in Example 3, (0.8 g, 3.2 mmol) in tetrahydrofuran (15 ml) added dropwise over 10 minutes. The reaction was stirred for 2 hours, quenched with ethanol (3 ml) and concentrated. The residue was triturated with ethyl ether and the organic phase was evaporated. The residue was chromatographed on silica gel eluted with chloroform and the fractions containing the product were combined, evaporated, dissolved in ethyl ether and treated with hydrogen chloride to give 7-chloro-3,4,5,6-tetrahydro-4-methyl-2-(2-methyl-1-propenyl)furo[4,3,2-ef][3]benzazepine hydrochloride: mp 270°–272° C. (dec).

Using the procedure of Example 12, replacing 7-chloro-3,4,5,6-tetrahydro-4-methylfuro[4,3,2-ef][3]benzazepine-2-methanol hydrochloride with 7-chloro-3,4,5,6-tetrahydro-4-methyl-2-(2-methyl-1-propenyl)-furo[4,3,2-ef][3]benzazepine hydrochloride gives 7-chloro-3,4,5,6-tetrahydro-4-methyl-2-(2-methylpropyl)-furo[4,3,2-ef][3]benzazepine hydrochloride.

EXAMPLE 15

Ethyl 7,9-Dichloro-3,4,5,6-tetrahydro-4-methylfuro[4,3,2-ef][3]benzazepine-2-carboxylate Using the general procedure of Example 1, replacing 4-chlorophenol with 2,4-dichlorophenol yields ethyl 7,9-dichloro-3,4,5,6-tetrahydro-4-methylfuro[4,3,2-ef][3]benzazepine-2-carboxylate hydrochloride.

EXAMPLE 16

Ethyl 7-Chloro-3,4,5,6-tetrahydro-4-methylfuro[4,3,2-ef][3]benzazepine-2-propanoate A 60% dispersion of sodium hydride in mineral oil (0.82 g, 20.5 mmol) was washed with hexane and suspended in ethyl ether (210 ml). The suspension was stirred under argon and treated with triethyl phosphonoacetate (4.5 g, 22 mmol). The resulting mixture was stirred for 1 hour and treated with a solution of 7-chloro-3,4,5,6-tetrahydro-4-methylfuro[4,3,2-ef][3]benzazepine-2-carboxaldehyde, prepared as in Example 3, (4.9 g, 20 mmol) in ethyl ether (250 ml). The reaction was stirred for 1.5 hours and quenched with water (25 ml). The organic phase was washed with water, dried with magnesium sulfate and concentrated to give a yellow solid which was slurried with hexane to give 5.2 g (81%) of ethyl (E)-3-(7-chloro-3,4,5,6-tetrahydro-4-methylfuro[4,3,2-ef][3]benzazepin-2-yl)-2-propenoate: mp 118°–121° C. The free base was treated with hydrogen chloride and recrystallized from ethanol to give the hydrochloride salt: mp >260° C. (dec).

Using the general procedure of Example 12, replacing 7-chloro-3,4,5,6-tetrahydro-4-methylfuro[4,3,2-ef][3]benzazepin-2-methanol hydrochloride with ethyl (E)-3-(7-chloro-3,4,5,6-tetrahydro-4-methylfuro-[4,3,2-ef][3]benzazepine-2-yl)-2-propenoate hydrochloride gave 0.15 g (49%) of ethyl 7-chloro-3,4,5,6-tetrahydro-4methylfuro[4,3,2-ef][3]benzazepine-2-propanoate hydrochloride: mp 170°–173° C.

EXAMPLE 17

7-Chloro-3,4,5,6-tetrahydro-4-methylfuro[4,3,2-ef][3]benzazepine-2-propanol

Using the general procedure of Example 2, replacing ethyl 7-chloro-3,4,5,6-tetrahydro-4-methylfuro[4,3,2-ef][3]benzazepine-2-carboxylate with ethyl 7-chloro 3,4,5,6-tetrahydro-4-methylfuro[4,3,2-ef][3]benzazepine-2-propanoate gave 1.9 g (76%) of 7-chloro-3,4,5,6-tetrahydro-4-methylfuro[4,3,2-ef][3]benzazepine-2-propanol hydrochloride: mp 208°–210° C.

EXAMPLE 18

7-Chloro-2-(3-chloropropyl)-3,4,5,6-tetrahydro-4-methylfuro[4,3,2-ef][3]benzazepine and 7-Chloro-3,4,5,6-tetrahydro-4-methyl-2-(2-propenyl)-furo[4,3,2-ef][3]benzazepine 7-Chloro-3,4,5,6-tetrahydro-4-methylfuro[4,3,2-ef][3]benzazepine-2-propanol hydrochloride, prepared as in Example 17, is treated with thionyl chloride and triethylamine in chloroform to give 7-chloro-2-(3-chloropropyl)-3,4,5,6-tetrahydro-4-methylfuro[4,3,2-ef][3]benzazepine hydrochloride.

7-Chloro-2-(3-chloropropyl)-3,4,5,6-tetrahydro-4-methylfuro[4,3,2-ef][3]benzazepine hydrochloride is converted to the free base and treated with lithium diisopropylamide in tetrahydrofuran to give 7-chloro-3,4,5,6-tetrahydro-4-methyl-2-(2-propenyl)furo-[4,3,2-ef][3]benzazepine.

EXAMPLE 19

7-Chloro-3,4,5,6-tetrahydro-α,α,4-trimethylfuro[4,3,2-ef][3]benzazepine-2-acetonitrile A solution of 7-chloro-3,4,5,6-tetrahydro-4methyl-furo[4,3,2-ef][3]benzazepine-2-methanol (0.01 mole), prepared as in Example 2, in thionyl chloride (30 ml) was heated to reflux under argon, cooled and concentrated to give 7-chloro-2-chloromethyl-3,4,5,6-tetrahydro-4-methylfuro[4,3,2-ef][3]benzazepine hydrochloride.

A mixture of 7-chloro-2-chloromethyl-3,4,5,6-tetrahydro-4-methylfuro[4,3,2-ef][3]benzazepine (5.0 mmol), potassium cyanide (10 mmol) and 18-crown-6 (0.1 mmol) in dry acetonitrile (25 ml) is stirred vigorously at room temperature. The reaction mixture is filtered and concentrated to one-third its volume, basified with 5% sodium bicarbonate and extracted with methylene chloride. The organic phase is dried and concentrated to give 7-chloro-3,4,5,6-tetrahydro-4-methylfuro[4,3,2-ef][3]benzazepine-2-acetonitrile.

A solution of 7-chloro-3,4,5,6-tetrahydro-4-methyl-furo[4,3,2-ef][3]benzazepine-2-acetonitrile (3.0 mmol) in anhydrous tetrahydrofuran (25 ml) at −78° is treated with lithium diisopropylamide (6.0 mmol). The mixture is stirred and treated with a solution of methyl iodide (6.0 mmol) in dry tetrahydrofuran (5 ml), added dropwise. The reaction mixture is stirred, quenched with water and concentrated. The resulting residue is extracted with ether and the organic phase is dried and concentrated to give 7-chloro-3,4,5,6-tetrahydro-α,α,4-trimethylfuro[4,3,2-ef][3]benzazepine-2-acetonitrile.

EXAMPLE 20

7-Chloro-3,4,5,6-tetrahydro-α,α,4-trimethylfuro[4,3,2-ef][3]benzazepine-2-butanenitrile Using the general procedure of Example 19, replacing 7-chloro-3,4,5,6-tetrahydro-4-methylfuro[4,3,2-ef][3]benzazepine-2-methanol with 7-chloro-3,4,5,6-tetrahydro-4-methylfuro[4,3,2-ef][3]benzazepine-2-propanol, prepared as in Example 17, gives 7-chloro-3,4,5,6-tetrahydro-α,α,4-trimethylfuro[4,3,2-ef][3]benzazepine-2-butanenitrile.

EXAMPLE 21

7-Chloro-3,4,5,6-tetrahydro-4-methyl-2-[(2-propenyloxy)methyl]furo[4,3,2-ef][3]benzazepine A 35% dispersion of potassium hydride in mineral oil (1 g, 8.3 mmol) in 1,2-dimethoxyethane (30 ml) was stirred and treated with a solution of 7-chloro-3,4,5,6-tetrahydro-4-methylfuro[4,3,2-ef][3]benzazepine-2-methanol, prepared as in Example 2, (2.1 g, 8.3 mmol) in 1,2-dimethoxyethane (35 ml). The mixture was stirred for 20 minutes under argon and treated with a solution of allyl iodide (1.4 g, 8.3 mmol) in 1,2-dimethoxyethane (5 ml) and stirred for 16 hours. The mixture was treated with water (3 ml), concentrated and extracted with ethyl ether. The organic phase was washed with water, dried with magnesium sulfate, concentrated and the residue chromatographed on silica gel eluted with a chloroformmethanol mixture (95:5). The fractions containing the product were pooled, concentrated and treated with hydrogen chloride. The crude hydrochloride salt was recrystallized from acetone to give 1.2 g (45%) of 7-chloro-3,4,5,6-tetrahydro-4-methyl-2-[(2-propenyloxy)methyl]furo[4,3,2-ef][3]benzazepine hydrochloride: mp 190°–193° C.

EXAMPLE 22

7-Chloro-3,4,5,6-tetrahydro-4-methyl-2-[(propyloxy)methyl]furo[4,3,2-ef][3]benzazepine Using the general procedure of Example 12, replacing 7-chloro-3,4,5,6-tetrahydro-4-methylfuro[4,3,2-ef][3]benzazepine-2-methanol hydrochloride with 7-chloro-3,4,5,6-tetrahydro-4-methyl-2-[(2-propenyloxy)methyl]furo[4,3,2-ef][3]benzazepine hydrochloride, prepared as in Example 19, gave, after recrystallization from acetone, 7-chloro-3,4,5,6-tetrahydro 4-methyl-2-[(propyloxy)methyl]furo[4,3,2-ef][3]benzazepine hydrochloride: mp 210°–211° C.

EXAMPLE 23

7-Chloro-3,4,5,6-tetrahydro-4-methyl-2-[(3-methyl-2-butenyloxy)methyl]furo[4,3,2-ef][3]benzazepine Using the procedure of Example 21, replacing allyl iodide with 3-methyl-2-butenyl bromide, gave 7-chloro-3,4,5,6-tetrahydro-4-methyl-2-[(3-methyl-2-butenyloxy)methyl]furo[4,3,2-ef][3]benzazepine hydrochloride: mp 170°–175° C.

EXAMPLE 24

7-Chloro-3,4,5,6-tetrahydro-4-methyl-2-[(2-propenylthio)methyl]furo[4,3,2-ef][3]benzazepine Using the general procedure of Example 11, replacing t-butyl 7-chloro-3,4,5,6-tetrahydro-4-methylfuro[4,3,2-ef][3]benzazepine-2-carboxylate with ethyl 7-chloro3,4,5,6-tetrahydro-4-methylfuro[4,3,2-ef][3]benzazepine-2carboxylate, prepared as in Example 1, gave, after recrystallization from ethanol, 2.85 g (53%) of ethyl 7-chloro-4-ethoxycarbonyl-3,4,5,6-tetrahydrofuro[4,3,2-ef][3]benzazepine-2-carboxylate: mp 175°–177° C.

A solution of ethyl 7-chloro-4-ethoxycarbonyl-3,4,5,6-tetrahydrofuro[4,3,2-ef][3]benzazepine-2-carboxylate (4 g, 14 mmol) in tetrahyrofuran (90 ml) was stirred under argon and treated with 2 M lithium borohydride in tetrahydrofuran (8.5 ml, 17 mmol) followed by trimethylborate (0.7 ml). The mixture was stirred for 18 hours, cooled, treated with 10% sodium hydroxide and concentrated. The residue was partitioned between water and ethyl ether and the organic phase was dried and concentrated to give 2.9 g (83%) of 7-chloro-4-ethoxycarbonyl-3,4,5,6-tetrahydrofuro[4,3,2-ef][3]benzazepine-2-methanol: mp 138°–143° C.

A solution of 7-chloro-4-ethoxycarbonyl-3,4,5,6-tetrahydrofuro[4,3,2-ef][3]benzazepine-2-methanol (1.7 g, 5.5 mmol) and carbon tetrabromide (2.4 g, 7.2 mmol) in methylene chloride (125 ml) was stirred at 0° C. and treated with triphenylphosphine (2.23 g, 8.5 mmol). The mixture was stirred for 20 minutes at 0° C., concentrated and the residue chromatographed on silica gel eluted with chloroform to give 1.2 g (60%) of 2-bromomethyl-7-chloro-4-ethoxycarbonyl-3,4,5,6-tetrahydrofuro[4,3,2-ef][3]benzazepine: mp 104°–109° C.

Using the general procedure of Example 21, replacing 7-chloro-3,4,5,6-tetrahydro-4-methylfuro[4,3,2-ef][3]benzazepine-2-methanol with allyl mercaptan and allyl iodide with 2-bromomethyl-7-chloro-4-ethoxycarbonyl 3,4,5,6-tetrahydrofuro[4,3,2-ef][3]benzazepine gave 0.55 g (56%) of 7-chloro-4-ethoxycarbonyl-3,4,5,6-tetrahydro-2-[(2-propenylthio)methyl]furo[4,3-,2ef-][3]benzazepine.

Using the general procedure of Example 11, replacing 7-chloro-4-ethoxycarbonyl-3,4,5,6-tetrahydro-[4,3,2-ef][3]benzazepine with 7-chloro-4-ethoxycarbonyl-3,4,5,6-tetrahydro-2-[(2-propylthio)methyl]furo[4,3,2-ef][3]benzazepine gave 7-chloro-3,4,5,6-tetrahydro-4-methyl-2-[(2-propenylthio)methyl]furo[4,3,2-ef][3]benzazepine hydrochloride: mp 190°–193° C.

EXAMPLE 25

2-Bromo-7-chloro-3,4,5,6-tetrahydro-4-methylfuro[4,3,2-ef][3]benzazepine

A solution of 7-chloro-3,4,5,6-tetrahydro-4-methylfuro[4,3,2-ef][3]benzazepine hydrobromide, prepared as in Example 11, (0.3 g, 1 mmol) in acetic acid (25 ml) and water (3 ml) was treated with bromine (0.16 g, 1 mmol) and stirred for 16 hours. The mixture was treated with bromine (0.08 g, 0.5 mmol) in acetic acid (1 ml), stirred and concentrated. The crude product was recrystallized from ethanol to give 0.2 g of 2-bromo-7-chloro-3,4,5,6-tetrahydro-4-methylfuro[4,3,2-ef]-[3]benzazepine hydrobromide: mp >280° C. (dec).

EXAMPLE 26

7-Chloro-3,4,5,6-tetrahydro-4-methyl-2-(trifluoromethyl)furo[4,3,2-ef][3]benzazepine A solution of 7-chloro-4-ethoxycarbonyl-3,4,5,6-tetrahydro[4,3,2-ef][3]benzazepine, prepared as in Example 11, (1.0 g, 3.6 mmol) in acetic acid (45 ml) was treated with a solution of bromine (0.6 g, 3.6 mmol) in acetic acid (5 ml). The mixture was stirred for three hours, filtered, and the filtrate concentrated. The residue was purified using silica gel flash chromatography (20% ethyl acetate in hexane) to give 0.60 g of 2-bromo-7-chloro-4-ethoxycarbonyl-3,4,5,6 tetrahydrofuro[4,3,2-ef][3]benzazepine: mp 115°–117° C.

A mixture of 2-bromo-7-chloro4-ethoxycarbonyl-3,4,5,6-tetrahydrofuro[4,3,2-ef][3]benzazepine (0.30 g, 0.84 mmol), trifluoromethyl iodide (0.66 g, 3.4 mmol) and activated copper powder (0.4 g) in dimethylformamide (10 ml) was heated in a stainless steel pressure vessel at 150° C. for 24 hours. The mixture was cooled and diluted with a mixture of water (50 ml) and ethyl acetate (100 ml). After filtering, the organic layer was washed with water (2×20 ml), dried over magnesium sulfate and concentrated. The residue was chromatographed on silica gel to give 0.06 g of 7-chloro-4-ethoxycarbonyl-2-trifluoromethyl-3,4,5,6-tetrahydrofuro[4,3,2-ef][3]benzazepine.

Using the general procedure of Example 11, replacing 7-chloro-4-ethoxycarbonyl-3,4,5,6-tetrahydrofuro-[4,3,2-ef][3]benzazepine with 7-chloro-4-ethoxycarbonyl-2-trifluoromethyl-3,4,5,6-tetrahydro[4,3,2-ef][3]benzazepine gave, after silica gel chromatography (25% ethyl acetate in hexane), 7-chloro-3,4,5,6-tetrahydro-4-methyl-2-(trifluoro-methyl)furo[4,3,2-ef][3]benzazepine hydrochloride: mp 256°–260° C.

EXAMPLE 27

7-Chloro-3,4,5,6-tetrahydrofuro-4-methyl-2-nitrofuro[4,3,2-ef][3]benzazepine

Using the general procedure of Example 25, replacing bromine with nitric acid gives 7-chloro-3,4,5,6-tetrahydro-4-methyl-2-nitrofuro[4,3,2-ef][3]benzazepine.

EXAMPLE 28

Ethyl 7-Chloro-3,4,5,6-tetrahydrofuro-[4,3,2-ef][3]benzazepine-2-carboxylate Using the general procedure of Example 24, replacing ethyl chloroformate with trichloroethyl chloroformate, gave (83%) of ethyl 7-chloro-3,4,5,6-tetrahydro-4-(trichloroethoxycarbonyl)furo[4,3,2-ef][3]benzazepine-2-carboxylate: mp 154°–156° C. A solution of ethyl 7-chloro-3,4,5,6-tetrahydro-4-(trichloroethoxycarbonyl)furo[4,3,2-ef][3]benzazepine-2-carboxylate (5.0 g, 11 mmol) in tetrahydrofuran (200 ml) and acetic acid (20 ml) was treated with powdered zinc (5.0 g) and stirred for 3 hours. The mixture was filtered and the filtrated concentrated. The residue was stirred with ethyl ether and basified with 10% sodium hydroxide. The mixture was filtered and the organic phase was dried with magnesium sulfate and concentrated to give 2.3 g (74%) of ethyl 7-chloro-3,4,5,6-tetrahydrofuro[4,3,2-ef]benzazepine-2-carboxylate: mp 112°–115° C.

EXAMPLE 29

7-Chloro-4-ethyl-3,4,5,6-tetrahydrofuro[4,3,2-ef][3]benzazepine-2-methanol

A solution of ethyl 7-chloro-3,4,5,6-tetrahydrofuro[4,3,2-ef][3]benzazepine-2-carboxylate, prepared as in Example 28, (0.75 g, 2.7 mmol) and triethylamine (3 ml) in dry tetrahydrofuran (25 ml) was stirred and treated with acetyl chloride (1.0 g, 12.7 mmol) in one portion. After 20 minutes, the reaction mixture was filtered, concentrated and the residue slurried in acetone. Filtration gave 0.54 g (75%) of ethyl 4-acetyl-7-chloro-3,4,5,6-tetrahydrofuro[4,3,2-ef][3]benzazepine-2-carboxylate: mp 154°–156° C.

A solution of ethyl 4-acetyl-7-chloro-3,4,5,6-tetrahydrofuro[4,3,2-ef][3]benzazepine-2-carboxylate (0.54 g, 1.67 mmol) in tetrahydrofuran (25 ml) was added dropwise to a stirred suspension of lithium aluminum hydride (0.126 g, 3.3 mmol) in ethyl ether (25 ml). Following work-up with water and aqueous sodium hydroxide, the product was purified by preparative thin-layer chromatography on silica gel developed with 10% ethanol in methylene chloride to give 0.16 g (22%) of 7-chloro-4-ethyl-3,4,5,6-tetrahydrofuro[4,3,2-ef][3]benzazepine-2-methanol as a colorless oil.

EXAMPLE 30

7-Chloro-4-ethyl-3,4,5,6-tetrahydrofuro[4,3,2-ef][3]benzazepine-2-carboxaldehyde Using the general procedure of Example 3, replacing 7-chloro-3,4,5,6-tetrahydro-4-methylfuro[4,3,2-ef][3]benzazepine-2-methanol with 7-chloro-4-ethyl-3,4,5,6-tetrahydrofuro[4,3,2-ef][3]benzazepine-2-methanol, prepared as in Example 27, gave 0.16 g (100%) of 7-chloro-4-ethyl-3,4,5,6-tetrahydrofuro[4,3,2-ef][3]benzazepine-2-carboxaldehyde: mp 60°–62° C.

EXAMPLE 31

7-Chloro-3,4,5,6-tetrahydro-2-methylfuro[4,3,2-ef][3]benzazepine and 7-Chloro-3,4,5,6-tetrahydro-2-methyl-4-(2-propenyl)-furo[4,3,2-ef][3]benzazepine Using the general procedure of Example 28, replacing ethyl 7-chloro-3,4,5,6-tetrahydro-4-methylfuro[4,3,2-ef][3]benzazepine-2-carboxylate with 7-chloro-3,4,5,6-tetrahydro-2,4-dimethylfuro[4,3,2-ef][3]benzazepine gives 7-chloro-3,4,5,6-tetrahydro-2-methyl-furo[4,3,2-ef][3]benzazepine.

A solution of 7-chloro-3,4,5,6-tetrahydro 2-methylfuro[4,3,2-ef][3]benzazepine in dry acetone is treated with potassium carbonate and allyl iodide to give 7-chloro-3,4,5,6-tetrahydro-2-methyl-4-(2-propenyl)-furo[4,3,2-ef][3]benzazepine.

EXAMPLE 32

Ethyl 3,4,5,6-Tetrahydro-4-methylfuro[4,3,2-ef][3]benzazepine-2-carboxylate

A mixture of ethyl 7-chloro-3,4,5,6-tetrahydro-4-methylfuro[4,3,2-ef][3]benzazepine-2-carboxylate hydrochloride, prepared as in Example 1, (6.2 g, 19 mmol) and 10% palladium on carbon (0.8 g) in absolute ethanol (200 ml) was shaken under hydrogen (40 psi) for 5 hours at 60° C. The mixture was cooled, filtered through an acid washed silicon dioxide filtration agent (Celite ®) and concentrated to give ethyl 3,4,5,6-tetrahydro-4-methylfuro[4,3,2-ef][3]benzazepine-2-carboxylate hydrochloride: mp > 200° C. (dec).

EXAMPLE 33

Ethyl 3,4,5,6-Tetrahydro-4-methyl-7-nitrofuro[4,3,2-ef][3]benzazepine-2-carboxylate A solution of ethyl 3,4,5,6-tetrahydro-4-methylfuro[4,3,2-ef][3]benzazepine-2-carboxylate hydrochloride, prepared as in Example 32, (5.7 g, 19 mmol) in sulfuric acid (40 ml) was stirred at 0° C. and treated with 70% nitric acid (1.7 g, 19 mmol). The mixture was stirred at 0° C. for 30 minutes and allowed to warm to 25° C. for 30 minutes. The mixture was poured onto ice, adjusted to pH 9 with solid sodium carbonate, diluted with methylene chloride (750 ml) and filtered. The organic phase was dried with magnesium sulfate and concentrated. The crude product was recrystallized from ethanol to give 1.9 g (33%) of ethyl 3,4,5,6-tetrahydro-4-methyl-7-nitrofuro[4,3,2-ef][3]benzazepine-2-carboxylate: mp 119°–121° C.

EXAMPLE 34

Ethyl 7-Amino-3,4,5,6-tetrahydro-4-methylfuro[4,3,2-ef][3]benzazepine-2-carboxylate Using the general procedure of Example 12, replacing 7-chloro-3,4,5,6-tetrahydro-4-methylfuro[4,3,2-ef][3]benzazepine-2-methanol hydrochloride with ethyl 3,4,5,6-tetrahydro-4-methyl-7-nitrofuro[4,3,2-ef][3]benzazepine-2-carboxylate, prepared as in Example 33, gave ethyl 7-amino-3,4,5,6-tetrahydro-4-methylfuro[4,3,2-ef][3]benzazepine-2-carboxylate: mp 115°–118° C.

EXAMPLE 35

Ethyl 7-Dimethylamino-3,4,5,6-tetrahydro-4-methylfuro[4,3,2-ef][3]benzazepine-2-carboxylate A suspension of ethyl 3,4,5,6-tetrahydro-4-methyl-7-nitrofuro[4,3,2-ef][3]benzazepine-2-carboxylate, prepared as in Example 33, (0.8 g, 2.6 mmol) in ethanol (200 ml) was treated with hydrogen chloride (0.7 g), 37% formalin (3 ml) and platinum oxide (150 mg). The mixture was shaken under hydrogen (40 psi) for 2 hours. The mixture was filtered, concentrated in vacuo and the residue was dissolved in toluene and concentrated in vacuo. The residue was dissolved in ethanol and treated with hydrogen chloride to give 0.7 g (70%) of ethyl 7-dimethylamino-3,4,5,6-tetrahydro-4-methylfuro[4,3,2-ef][3]benzazepine-2-carboxylate dihydrochloride: mp >220° C. (d).

EXAMPLE 36

3,4,5,6-Tetrahydro-4-methylfuro[4,3,2-ef][3]benzazepine-2-methanol

Using the general procedure of Example 2, replacing ethyl 7-chloro-3,4,5,6-tetrahydro-4-methylfuro[4,3,2-ef][3]benzazepine-2-carboxylate with ethyl 3,4,5,6-tetrahydro-4-methylfuro[4,3,2-ef][3]benzazepine-2-carboxylate, prepared as in Example 32, gave, after recrystallization from acetone, 0.6 g of 3,4,5,6-tetrahydro-4-methylfuro[4,3,2-ef][3]benzazepine-2-methanol hydrochloride: mp 216°–218° C.

EXAMPLE 37

Ethyl 7-Fluoro-3,4,5,6-tetrahydro-4-methylfuro[4,3,2-ef][3]benzazepine-2-carboxylate,

7-Fluoro-3,4,5,6-tetrahydro-4-methylfuro[4,3,2-ef][3]benzazepine-2-methanol, and

7-Fluoro-3,4,5,6-tetrahydro-4-methylfuro[4,3,2-ef][3]benzazepine-2-carboxaldehyde Using the general procedure of Example 1, replacing 4-chlorophenol with 4-fluorophenol gives ethyl 7-fluoro-3,4,5,6-tetrahydro-4-methylfuro[4,3,2-ef][3]benzazepine-2-carboxylate.

Using the general procedure of Example 2, replacing ethyl 7-chloro-3,4,5,6-tetrahydro-4-methylfuro[4,3,2-ef][3]benzazepine-2-carboxylate with ethyl 7-fluoro-3,4,5,6-tetrahydro-4-methylfuro[4,3,2-ef][3]benzazepine-2-carboxylate gives 7-fluoro-3,4,5,6-tetrahydro-4-methylfuro[4,3,2-ef][3]benzazepine-2-methanol.

Alternatively, using the general procedure of Example 11, replacing t-butyl 7-chloro-3,4,5,6-tetrahydro-4-methylfuro[4,3,2-ef][3]benzazepine-2-carboxylate with ethyl 3,4,5,6-tetrahydro-4-methyl-7-nitrofuro[4,3,2-ef][3]benzazepine-2-carboxylate, prepared as in Example 33, gave ethyl 4-ethoxycarbonyl-3,4,5,6-tetrahydro-7-nitrofuro[4,3,2-ef][3]benzazepine-2-carboxylate: mp 172°–173° C.

Using the general procedure of Example 34, replacing ethyl 3,4,5,6-tetrahydro-4-methyl-7-nitrofuro[4,3,2-ef][3]benzazepine-2-carboxylate with ethyl 4-ethoxycarbonyl-3,4,5,6-tetrahydro-7-nitrofuro[4,3,2-ef][3]benzazepine-2-carboxylate gave ethyl 7-amino-4-ethoxycarbonyl- 3,4,5,6-tetrahydrofuro[4,3,2-ef][3]benzazepine-2-carboxylate: mp 142°–144° C.

A suspension of ethyl 7-amino-4-ethoxycarbonyl-3,4,5,6-tetrahydrofuro[4,3,2-ef][3]benzazepine-2-carboxylate (0.9 g, 2.7 mmol) in ethanol (8 ml) was stirred at 5° C. and treated with 60% fluoboric acid (2.25 ml). The mixture was stirred for 10 minutes, treated with butyl nitrite (0.45 g), stirred for 30 minutes and allowed to stand at 0° C. for 4 hours. The solution was diluted with ethyl ether (250 ml) and allowed to stand at 3° C. for 16 hours. The organic phase was decanted from the resulting mixture and the residue dissolved in methylene chloride and concentrated in vacuo to give 2,4-bis-(ethoxycarbonyl)-3,4,5,6-tetrahydrofuro[4,3,2 ef][3]benzazepine-7-diazonium tetrafluoroborate.

2,4-Bis(ethoxycarbonyl)-3,4,5,6-tetrahydrofuro-[4,3,2 ef][3]benzazepine-7-diazonium tetrafluoroborate (0.95 g, 2.2 mmol) was heated at 145°–150° C. under argon for 45 minutes. The residue was slurried with ethyl ether and filtered. The filtrate was concentrated in vacuo and the residue recrystallized from ethanol to give ethyl 4-ethoxycarbonyl-7-fluoro-3,4,5,6-tetrahydrofuro[4,3,2-ef][3]benzazepine-2-carboxylate: mp 142°–143° C.

Using the general procedure of Example 2, replacing ethyl 7-chloro-3,4,5,6-tetrahydro-4-methylfuro[4,3,2-ef][3]benzazepine-2-carboxylate with ethyl 4-ethoxycarbonyl-7-fluoro-3,4,5,6-tetrahydrofuro[4,3,2-ef][3]benzazepine-2-carboxylate gave 7-fluoro-3,4,5,6-tetrahydro-4-methylfuro[4,3,2-ef][3]benzazepine-2-methanol hydrochloride: mp>228° C.

Using the general procedure of Example 3, replacing 7-chloro-3,4,5,6-tetrahydro-4-methylfuro[4,3,2-ef][3]benzazepine-2-methanol with 7-fluoro-3,4,5,6-tetrahydro-4-methylfuro[4,3,2-ef][3]benzazepine-2-methanol gives 7-fluoro-3,4,5,6-tetrahydro-4-methylfuro[4,3,2-ef][3]benzazepine-2-carboxaldehyde.

EXAMPLE 38

Ethyl 7-Bromo-3,4,5,6-tetrahydro-4-methylfuro[4,3,2-ef][3]benzazepine-2-carboxylate Using the general procedure of Example 1, replacing 4-chlorophenol with 4-bromophenol gives ethyl 7-bromo-3,4,5,6-tetrahydro-4-methylfuro[4,3,2-ef][3]-benzazepine-2-carboxylate.

Alternatively, using the general procedure of Example 39, replacing hydrochloric acid with hydrobromic acid and sodium cyanide/cuprous cyanide with cuprous bromide gave ethyl 7-bromo-3,4,5,6-tetrahydro-4-methylfuro[4,3,2-ef][3]benzazepine-2-carboxylate: mp 90°–92° C.

EXAMPLE 39

Ethyl 7-Cyano-3,4,5,6-tetrahydro-4-methylfuro[4,3,2-ef][3]benzazepine-2-carboxylate,

7-Cyano-3,4,5,6-tetrahydro-4-methylfuro[4,3,2-ef][3]benzazepine-2-methanol, and

7-Cyano-3,4,5,6-tetrahydro-4-methylfuro[4,3,2-ef][3]benzazepine-2-carboxaldehyde Ethyl 7-amino-3,4,5,6-tetrahydro-4-methylfuro[4,3,2-ef][3]benzazepine-2-carboxylate (0.22 g, 0.8 mmol), prepared as in Example 34, was dissolved in a mixture of water (6 ml) and 3N hydrochloric acid (3.1 ml) at 0° C. This solution was treated dropwise with a solution of sodium nitrate (0.126 g, 1.8 mmol) in water (6 ml). After ten minutes the resulting solution containing the diazonium salt was added dropwise to a mixture of toluene (15 ml) and a solution of sodium cyanide (0.3 g, 6.1 mmol) and cuprous cyanide (0.12 g, 1.3 mmol) in water (10 ml) at 60° C. The resulting suspension was stirred for 30 minutes, cooled, and basified with saturated sodium bicarbonate (10 ml). The aqueous layer was extracted with toluene and the combined organic layers dried over magnesium sulfate. The solvent was distilled and the residue purified using silica gel chromatography (5% ethanol in methylene chloride) to give 7-cyano-3,4,5,6-tetrahydro-4-methylfuro[4,3,2-ef][3]-benzazepine-2-carboxylate. The free base was treated with hydrogen chloride to give 7-cyano-3,4,5,6-tetrahydro-4-methylfuro[4,3,2-ef][3]benzazepine-2-carboxylate hydrochloride: mp>258° C.

Using the general procedure of Example 24, replacing ethyl 7-chloro-4-ethoxycarbonyl-3,4,5,6-tetrahydrofuro[4,3,2-ef][3]benzazepine-2-carboxylate with ethyl 7-cyano-3,4,5,6-tetrahydro-4-methylfuro-[4,3,2-ef][3]benzazepine-2-carboxylate gives 7-cyano-3,4,5,6-tetrahydro-4-methylfuro[4,3,2-ef][3]benzazepine-2-methanol.

Using the general procedure of Example 3, replacing 7-chloro-3,4,5,6-tetrahydro-4-methylfuro[4,3,2-ef][3]benzazepine-2-methanol with 7-cyano-3,4,5,6-tetrahydro-4-methylfuro[4,3,2-ef][3]benzazepine-2-methanol gives 7-cyano-3,4,5,6-tetrahydro-4-methyl-furo[4,3,2-ef][3]-benzazepine-2-carboxaldehyde.

EXAMPLE 40

Ethyl 9-Chloro-3,4,5,6-tetrahydro-4-methylfuro[4,3,2-ef][3]benzazepine-2-carboxylate, 9-Chloro-3,4,5,6-tetrahydro-4-methylfuro[4,3,2-ef][3]benzazepine-2-methanol, and 9-Chloro 3,4,5,6 tetrahydro-4-methylfuro[4,3,2-ef[3]benzazepine-2-carboxaldehyde Using the general of procedure of Example 37, replacing 4-fluorophenol with 2-chlorophenol gives ethyl 9-chloro-3,4,5,6-tetrahydro-4-methylfuro[4,3,2-ef][3]-benzazepine-2-carboxylate, 9-chloro-3,4,5,6-tetrahydro-4-methylfuro[4,3,2-ef][3]benzazepine-2-methanol and 9-chloro-3,4,5,6-tetrahydro-4-methylfuro[4,3,2-ef][3]-benzazepine-2-carboxaldehyde.

EXAMPLE 41

7-Chloro-3,4,5,6-tetrahydro-N,N,4-trimethylfuro[4,3,2-ef][3]benzazepine-2-sulfonamide 7-Chloro-3,4,5,6-tetrahydro-4-methylfuro[4,3,2-ef][3]benzazepine, prepared as in Example 11, is treated with excess chlorosulfonic acid and the mixture is carefully poured into ice water and carefully treated with dimethylamine to give 7-chloro-3,4,5,6-tetrahydro-N,N,4-trimethylfuro[4,3,2-ef][3]benzazepine-2-sulfonamide.

EXAMPLE 42

Diethyl (7-Chloro-3,4,5,6-tetrahydro-4-methylfuro-[4,3,2-ef][3]benzazepine-2-yl)phosphonate 2-Bromo-7-chloro-3,4,5,6-tetrahydro-4-methylfuro[4,3,2-ef][3]benzazepine, prepared as in Example 25, is treated with butyllithium in ethyl ether and then with diethyl chlorophosphate to give diethyl (7-chloro-[3,4,5,6-tetrahydro-4-methylfuro[4,3,2-ef][3]benzazepine-2-yl)phosphonate.

EXAMPLE 43

7-Chloro-3,4,5,6-tetrahydro-4-methyl-2-(methylthio)-furo[4,3,2-ef][3]benzazepine Sec-butyllithium in hexane (1.3M, 1.3 ml, 1.7 mmol) was added to a solution of 2-bromo-7-chloro-3,4,5,6-tetrahydro-4-methylfuro[4,3,2-ef][3]benzazepine, prepared as in Example 25, (0.5 g, 1.7 mmol) in tetrahydrofuran (10 ml) stirred at −78° C. under argon.

The resulting mixture is treated with dimethyl disulfide to give 7-chloro-3,4,5,6-tetrahydro-4-methyl-2-(methylthio)furo[4,3,2-ef][3]benzazepine.

EXAMPLE 44

7-Chloro-3,4,5,6-tetrahydro-4-methyl-2-phenyl-furo[4,3,2-ef][3]benzazepine

Using the general procedure of Example 43, replacing methyl disulfide with tributyltin chloride gives tributyl-[2-(7-chloro-3,4,5,6-tetrahydro-4-methylfuro[4,3,2-ef][3]benzazepin-2-yl)]stannane. The tributyl-[2-(7-chloro-3,4,5,6-tetrahydro-4-methylfuro[4,3,2-ef][3]benzazepin-2-yl)]stannane is treated with iodobenzene and bis(triphenylphosphine)palladium(II) chloride to give chloro 3,4,5,6-tetrahydro-4-methyl-2-phenyl-furo[4,3,2-ef][3]benzazepine.

EXAMPLE 45

7-Chloro-3,4,5,6-tetrahydro-α,4-dimethylfuro[4,3,2 ef][3]benzazepine-2-methanol

Sodium borohydride is added to a solution of 2-acetyl-7-chloro-3,4,5,6-tetrahydro-4-methylfuro[4,3,2-ef][3]benzazepine, prepared as in Example 10, in methanol stirred at 0° C. The mixture is stirred for 2 hours, diluted with water and extracted with ethyl ether. The organic phase is dried with magnesium sulfate and concentrated in vacuo to give 7-chloro-3,4,5,6-tetrahydro-α,4-dimethylfuro[4,3,2-ef][3]benzazepine-2-methanol.

EXAMPLE 46

7-Chloro-3,4,5,6-tetrahydro-α,α,4-trimethylfuro[4,3,2-ef][3]benzazepine-2-methanol Methylmagnesium bromide in tetrahydrofuran is added to a solution of ethyl 7-chloro-3,4,5,6-tetrahydro-4-methylfuro[4,3,2-ef][3]benzazepine-2-carboxylate, prepared as in Example 1, in tetrahydrofuran stirred under argon. The mixture is stirred for 1 hour, basified with ammonium hydroxide and extracted with ethyl ether. The organic phase was dried with magnesium sulfate and concentrated in vacuo to give an oil which is chromatographed on silica gel eluted with methanol-methylene chloride to give 7-chloro-3,4,5,6-tetrahydro-α,α,4-trimethylfuro-[4,3,2-ef][3]benzazepine-2-methanol.

EXAMPLE 47

7-Chloro-2-[[4-(chlorophenyl)methyloxy]methyl]]-3,4,5,6-tetrahydro-4-methylfuro[4,3,2-ef][3]benzazepine Using the general procedure of Example 21, replacing allyl iodide with 4-chlorobenzyl chloride gave 7-chloro-2-[[4-(chlorophenyl)methyloxy]methyl]]-3,4,5,6-tetrahydro-4-methylfuro[4,3,2-ef][3]benzazepine hydrochloride: mp 97° C.

EXAMPLE 48

7-Chloro-3,4,5,6-tetrahydro-4-methylfuro[4,3,2-ef][3]benzazepine-2-carboxamide,

N-Butyl-7-chloro-3,4,5,6-tetrahydro-4-methylfuro[4,3,2-ef][3]benzazepine-2-carboxamide, 7-Chloro-3,4,5,6-tetrahydro-4-methyl-N-(phenylmethyl)furo[4,3,2-ef][3]benzazepine-2-carboxamide, 7-Chloro-3,4,5,6-tetrahydro-4-methyl-N-(2-phenylethyl)furo[4,3,2-ef][3]benzazepine-2-carboxamide, 7-Chloro-3,4,5,6-tetrahydro-N,4-dimethyl-N-(2-phenylethyl)furo[4,3,2-ef][3]benzazepine-2-carboxamide, and 7-Chloro-3,4,5,6-tetrahydro-4-methyl-N-(3-phenylpropyl)furo[4,3,2-ef][3]benzazepine-2-carboxamide Using the general procedure of Example 8, replacing dimethylamine with ammonia, butylamine, benzylamine, phenethylamine, N-methylphenethylamine or 3-phenyl-1-propylamine gave, respectively:
7-chloro-3,4,5,6-tetrahydro-4-methylfuro[4,3,2-ef][3]benzazepine-2-carboxamide: mp 230° C.,
N-butyl-7-chloro-3,4,5,6-tetrahydro-4-methylfuro[4,3,2-ef][3]benzazepine-2-carboxamide: mp 111° C.,
7-chloro-3,4,5,6-tetrahydro-4-methyl-N-(phenylmethyl)furo[4,3,2-ef][3]benzazepine-2-carboxamide: mp 147° C.,
7-chloro-3,4,5,6-tetrahydro-4-methyl-N-(2-phenylethyl)furo[4,3,2-ef][3]benzazepine-2-carboxamide: mp 138.5°-139.5° C.,
7-chloro-3,4,5,6-tetrahydro-N,4-dimethyl-N-(2-phenylethyl)furo[4,3,2-ef][3]benzazepine-2-carboxamide hydrochloride: mp 225° C., and
7-chloro-3,4,5,6-tetrahydro-4-methyl-N-(3-phenylpropyl)furo[4,3,2-ef][3]benzazepine-2-carboxamide hydrochloride: mp 244°-246° C.

EXAMPLE 49

Phenylmethyl 7-Chloro-3,4,5,6-tetrahydro-4-methylfuro[4,3,2-ef][3]benzazepine-2-propanoate A solution of ethyl 3-(7-chloro-3,4,5,6-tetrahydro-4-methylfuro[4,3,2-ef][3]benzazepin-2-yl)-2-propenoate, prepared as in Example 16, in benzyl alcohol (2 ml) was treated with a 60% dispersion of sodium hydride in mineral oil (14 mg) and stirred for 16 hours. The mixture was filtered and the filter cake dried to give phenylmethyl (E)-3-(7-chloro-3,4,5,6-tetrahydro-4-methylfuro[4,3,2-ef][3]benzazepin-2-yl)-2-propenoate: mp 240° C.

Using the general procedure of Example 16, replacing ethyl (E)-3-(7-chloro-3,4,5,6-tetrahydro-4-methylfuro[4,3,2-ef][3]benzazepin-2-yl)-2-propenoate hydrochloride with phenylmethyl (E)-3-(7-chloro-3,4,5,6-tetrahydro-4-methylfuro[4,3,2-ef][3]benzazepin-2-yl)-2-propenoate hydrochloride gave phenylmethyl 7-chloro-3,4,5,6-tetrahydro-4-methylfuro[4,3,2-ef][3]benzazepine-2-propanoate hydrochloride: mp 172° C. (d).

EXAMPLE 50

2,7-Dichloro-3,4,5,6-tetrahydro-4-methylfuro[4,3,2-ef][3]benzazepine

Sec-butyllithium in hexane (1.3M, 1.3 ml, 1.7 mmol) was added to a solution of 2-bromo-7-chloro-3,4,5,6-tetrahydro-4-methylfuro[4,3,2-ef][3]benzazepine, prepared as in Example 25, (0.5 g, 1.7 mmol) in tetrahydrofuran (10 ml) stirred at −78° C. under argon. The solution was stirred to 10 minutes and treated with a solution of N-chlorosuccinimide (0.24 g, 1.8 mmol) in tetrahydrofuran (5 ml), stirred for 15 minutes, allowed to warm to 25° C. and stirred for 45 minutes. The mixture was treated with water, concentrated in vacuo and partitioned between ethyl ether and water. The organic phase was dried with magnesium sulfate and concentrated in vacuo. The residue was chromatographed on preparative silica gel plates eluted with ethanol-methylene chloride to give 0.2 g of 2,7-dichloro-3,4,5,6-tetrahydro-4-methylfuro[4,3,2-ef][3]benzazepine: mp 56°-58° C., which was dissolved in ethyl ether and treated with hydrogen chloride to give 0.16 g (33%) of 2,7-dichloro-3,4,5,6-tetrahydro-4-methylfuro[4,3,2-ef][3]benzazepine hydrochloride: mp>338° C.

EXAMPLE 51

Ethyl 7-chloro-3,4,5,6-tetrahydro-4-methyl-9-nitrofuro[4,3,2-ef][3] benzazepine-2-carboxylate Using the general procedure of Example 33, replacing ethyl 3,4,5,6-tetrahydro-4-methylfuro[4,3,2-ef][3]benzazepine-2-carboxylate hydrochloride with ethyl 7-chloro-3,4,5,6-tetrahydro-4-methylfuro[4,3,2-ef][3]benzazepine-2-carboxylate hydrochloride, prepared as in Example 1, gave ethyl 7-chloro-3,4,5,6-tetrahydro-4-methyl-9-nitrofuro[4,3,2-ef][3]benzazepine-2-carboxylate: mp 124°-125° C.

EXAMPLE 52

Ethyl 9-Amino-7-chloro-3,4,5,6-tetrahydro-4-methylfuro[4,3,2-ef][3]benzazepine-2-carboxylate Using the general procedure of Example 34, replacing ethyl 3,4,5,6-tetrahydro-4-methyl-7-nitrofuro[4,3,2-ef][3]benzazepine-2-carboxylate with ethyl 7-chloro-3,4,5,6-tetrahydro-4-methyl-9-nitrofuro[4,3,2-ef][3]benzazepine-2-carboxylate, prepared as in Example 51, gave ethyl 9-amino-7-chloro-3,4,5,6-tetrahydro-4-methylfuro[4,3,2-ef][3]benzazepine-2-carboxylate; mp 172°-175° C.

EXAMPLE 53

Ethyl 7,9-Dichloro-3,4,5,6-tetrahydro-4-methylfuro[4,3,2-ef][3]benzazepine-2-carboxylate Using the general procedure of Example 39, replacing ethyl 7-amino-3,4,5,6-tetrahydro-4-methylfuro[4,3,2-ef][3]benzazepine-2-carboxylate with ethyl 9-amino-7-chloro-3,4,5,6-tetrahydro-4-methylfuro[4,3,2-ef][3benzazepine-2-carboxylate, prepared as in Example 52, and sodium cyanide/cuprous cyanide with cuprous chloride gave ethyl 7,9-dichloro-3,4,5,6-tetrahydro-4-methylfuro[4,3,2-ef][3]benzazepine-2-carboxylate hydrochloride: mp>247° C.

EXAMPLE 54

Ethyl 7-Chloro-3,4,5,6-tetrahydro-4-methyl-9-(methylamino)-furo[4,3,2-ef][3]benzazepine-2-carboxylate and Ethyl 7-Chloro-9-dimethylamino-3,4,5,6-tetrahydro-4-methylfuro[4,3,2-ef][3]benzazepine-2-carboxylate Using the general procedure of Example 35, replacing ethyl 3,4,5,6-tetrahydro-4-methyl-7-nitrofuro[4,3,2-ef][3]benzazepine-2-carboxylate with ethyl 7-chloro-3,4,5,6-tetrahydro-4-methyl-9-nitrofuro[4,3,2-ef][3]benzazepine-2-carboxylate, prepared as in Example 51, gave a mixture that was chromatographed on preparative silica gel plates eluted with ethyl acetate-hexane (1:1) to give:

ethyl 7-chloro-3,4,5,6-tetrahydro-4-methyl-9-(methylamino)furo[4,3,2-ef][3]benzazepine-2-carboxylate hydrochloride: mp>240° C. (d) and ethyl 7-chloro-9-dimethylamino-3,4,5,6-tetrahydro-4-methylfuro[4,3,2-ef][3]benzazepine-2-carboxylate hydrochloride: mp 125°–127° C.

EXAMPLE 55

7-Dimethylamino-3,4,5,6-tetrahydro-4-methyl-furo[4,3,2-ef][3]benzazepine-2-methanol, 7-Bromo-3,4,5,6-tetrahydro-4-methylfuro[4,3,2-ef][3]benzazepine-2-methanol, and 7-Chloro-9-dimethylamino-3,4,5,6-tetrahydro-4-methylfuro[4,3,2-ef][3]benzazepine-2-methanol Using the general procedure of Example 2, replacing ethyl 7-chloro-3,4,5,6-tetrahydro-4-methylfuro[4,3,2-ef][3]benzazepine-2-carboxylate with ethyl 7-dimethylamino-3,4,5,6-tetrahydro-4-methylfuro[4,3,2-ef][3]benzazepine- 2-carboxylate, prepared as in Example 35, ethyl 7-bromo-3,4,5,6-tetrahydro-4-methylfuro[4,3,2-ef][3]benzazepine-2-carboxylate, prepared in Example 38, or ethyl 7-chloro-9-dimethylamino-3,4,5,6-tetrahydro-4-methylfuro[4,3,2-ef][3]benzazepine-2-carboxylate, prepared in Example 54, gave, respectively:

7-dimethylamino-3,4,5,6-tetrahydro-4-methyl-furo[4,3,2-ef][3]benzazepine-2-methanol dihydrochloride: mp>215° C., 7-bromo-3,4,5,6-tetrahydro-4-methylfuro[4,3,2-ef][3]benzazepine-2-methanol hydrochloride: mp>228° C., and 7-chloro-9-dimethylamino-3,4,5,6-tetrahydro-4-methylfuro[4,3,2-ef][3]benzazepine-2-methanol hydrochloride hydrate: mp>145° C.

EXAMPLE 56

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| 7-Chloro-2-ethyl-3,4,5,6-tetrahydro-4-methylfuro[4,3,2-ef][3]benzazepine | 50 mg |
| magnesium stearate | 5 mg |
| lactose | 75 mg |

EXAMPLE 57

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 7-Chloro-3,4,5,6-tetrahydro-4-methylfuro[4,3,2-ef][3]benzazepine-2-propanol | 100 mg |
| calcium sulfate dihydrate | 150 mg |
| sucrose | 20 mg |
| starch | 10 mg |
| talc | 5 mg |
| stearic acid | 3 mg |

EXAMPLE 58

7-Chloro-3,4,5,6-tetrahydro-4-methyl-2-[(2-propenyloxy)methyl]furo[4,3,2-ef][3]benzazepine, 75 mg, is dispersed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, the invention is not limited to the precise instructions herein disclosed and that the right to all modifications coming within the scope of the following claims is reserved.

What is claimed is:

1. A compound represented by the formula:

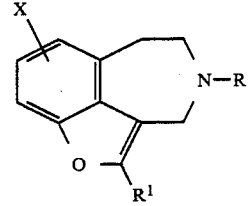

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}PH$, $SCF_3$, or any accessible combination thereof of up to three substituents;

R is H, $C_{1-6}$alkyl, or $C_{3-5}$alkenyl;

$R^1$ is W, $(CH_2)_{0-2}CWYZ$, or $C_{3-5}$ alkenyl, except where the double bond is in the 1-position;

$R^{10}$ is $C_{1-6}$alkyl or $(CH_2)_{0-6}PH$;

$R^{11}$ and $R^{16}$ independently are H, $C_{1-6}$alkyl, or $(CH_2)_{0-6}PH$;

$R^{12}$ is H, $C_{1-6}$alkyl, $COR^{14}$, or $SO_2R^{15}$;

each $R^{13}$ independently is H or $C_{1-6}$alkyl;

$R^{14}$ and $R^{15}$ independently are $C_{1-6}$alkyl or $(CH_2)_{0-6}PH$;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}PH$;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$PH; and $R^5$ and $R^6$ independently are $C_{1-6}$alkyl, $C_{3-5}$alkenyl, or $(CH_2)_{0-6}$PH; where pH represents unsubstituted phenyl or phenyl substituted by up to three substituents selected from $C_{1-6}$alkyl, $C_{1-6}$alkoxy, halo, $CF_3$ or CN; or a pharmaceutically acceptable salt thereof.

2. A compound represented by the formula:

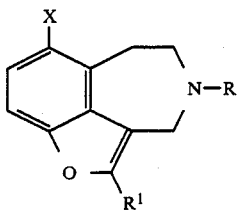

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$PH, or $SCF_3$;

R is H, $C_{1-6}$alkyl, or $C_{3-5}$alkenyl;

$R^1$ is W, $(CH_2)_{0-2}CWYZ$, or $C_{3-5}$ alkenyl, except where the double bond is in the 1-position;

$R^{10}$ is $C_{1-6}$alkyl or $(CH_2)_{0-6}$PH;

$R^{11}$ and $R^{16}$ independently are H, $C_{1-6}$alkyl, or $(CH_2)_{0-6}$PH;

$R^{12}$ is H, $C_{1-6}$alkyl, $COR^{14}$, or $SO_2R^{15}$;

each $R^{13}$ independently is H or $C_{1-6}$alkyl;

$R^{14}$ and $R^{15}$ independently are $C_{1-6}$alkyl or $(CH_2)_{0-6}$PH;

W is H, $NO_2$, $C_{1-6}$alkyl, $CH_2CH_2OH$, CN, $C(R^{13})_2(OR^2)$, $CH_2SR^2$, $COR^2$, $CO_2R^2$, $CONR^3R^4$, $SO_2NR^3R^4$, $SO_3R^2$, $SO_2R^5$, $SOR^5$, $SR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, Cl, Br, F, I, $CF_3$, or $(CH_2)_{0-6}$PH;

Y and Z independently are H or $C_{1-6}$alkyl;

$R^2$, $R^3$, and $R^4$ independently are H, $C_{1-6}$alkyl, $C_{3-5}$alkenyl, or $(CH_2)_{0-6}$PH; where pH represents unsubstituted phenyl or phenyl substituted by up to three substituents selected from $C_{1-6}$ alkyl, $C_{1-6}$ alkoxy, halo, $CF_3$ or CN; and $R^5$ and $R^6$ independently are $C_{1-6}$alkyl, $C_{3-5}$alkenyl, or $(CH_2)_{0-6}$PH; or a pharmaceutically acceptable salt thereof.

3. A compound of claim 1 wherein X is one or two substituents selected from the group consisting of Cl, Br, F, I, CN, or $NR^{12}R^{13}$.

4. A compound of claim 3 wherein R is $CH_3$ or H, and X is at position 7 or 7,9.

5. A compound of claim 4 that is 7-chloro-3,4,5,6-tetrahydro-2,4-dimethylfuro[4,3,2-ef][3]benzazepine, or a pharmaceutically acceptable salt thereof.

6. A compound of claim 4 that is 2-bromo-7-chloro-3,4,5,6-tetrahydro-4-methylfuro[4,3,2-ef][3]benzazepine, or a pharmaceutically acceptable salt thereof.

7. A compound of claim 4 that is:
ethyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-methanol;
7-chloro-3,4,5,6-tetrahydro-4-methylfuro[4,3,2-ef][3]benzazepine-2-carboxaldehyde;
methyl 7-chloro-3,4,5,6 tetrahydro-4-methylfuro[4,3,2-ef][3]benzazepine-2-carboxylate;
2-propenyl-7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-carbonitrile;
7-chloro-3,4,5,6-tetrahydro-4-methylfuro[4,3,2-ef][3]benzazepine;
7-chloro-2-ethyl-3,4,5,6-tetrahydro-4-methylfuro[4,3,2-ef][3]benzazepine;
ethyl 7-chloro-3,4,5,6-tetrahydro-4-methylfuro[4,3,2-ef][3]benzazepine-2-propanoate;
7-chloro-3,4,5,6-tetrahydro-4-methylfuro[4,3,2-ef][3]benzazepine-2-propanol;
7-chloro-3,4,5,6-tetrahydro-4-methyl-2-[(2-propenyloxy)methyl]furo[4,3,2-ef][3]benzazepine;
7-chloro-3,4,5,6-tetrahydro-4-methyl-2-[(propyloxy)methyl]furo[4,3,2-ef][3]benzazepine;
7-chloro-3,4,5,6-tetrahydro-4-methyl-2-[(3-methyl-2-butenyloxy)methyl]furo[4,3,2-ef][3]benzazepine;
7-chloro-3,4,5,6-tetrahydro-4-methyl-2-[(2-propenylthio)methyl]furo[4,3,2-ef][3]benzazepine;
7-chloro-3,4,5,6-tetrahydro-4-methyl-2-(trifluoromethyl)furo[4,3,2-ef][3]benzazepine;
7-chloro-3,4,5,6-tetrahydro-4-methylfuro[4,3,2-ef][3]benzazepine-2-carboxamide;
N-butyl-7-chloro-3,4,5,6-tetrahydro-4-methylfuro[4,3,2-ef][3]benzazepine-2-carboxamide;
N,N-dimethyl-7-chloro-3,4,5,6-tetrahydro-4-methylfuro[4,3,2-ef][3]benzazepine-2-carboxamide;
7-chloro-3,4,5,6-tetrahydro-4-methyl-N-(phenylmethyl)furo[4,3,2-ef][3]benzazepine-2-carboxamide;
7-chloro-3,4,5,6-tetrahydro-4-methyl-N-(2-phenylethyl)furo[4,3,2-ef][3]benzazepine-2-carboxamide;
7-chloro-3,4,5,6-tetrahydro-N,4-dimethyl-N-(2-phenylethyl)furo[4,3,2-ef][3]benzazepine-2-carboxamide;
7-chloro-3,4,5,6-tetrahydro-4-methyl-N-(3-phenylpropyl)furo[4,3,2-ef][3]benzazepine-2-carboxamide;
phenylmethyl-7-chloro-3,4,5,6-tetrahydro-4-methylfuro[4,3,2-ef][3]benzazepine-2-propanoate;
2,7-dichloro-3,4,5,6-tetrahydro-4-methylfuro[4,3,2-ef][3]benzazepine;
7-chloro-2-[(4-chlorophenyl)methyloxy]-3,4,5,6-tetrahydro-4-methylfuro[4,3,2-ef][3]benzazepine;
7-fluoro-3,4,5,6-tetrahydro-4-methylfuro[4,3,2-ef][3]benzazepine-2-methanol;
7-chloro-9-dimethylamino-3,4,5,6-tetrahydro-4-methylfuro[4,3,2-ef][3]benzazepine-2-methanol;
7-bromo-3,4,5,6-tetrahydro-4-methylfuro[4,3,2-ef][3]benzazepine-2-methanol;
7-dimethylamino-3,4,5,6-tetrahydro-4-methylfuro[4,3,2-ef][3]benzazepine-2-methanol;
ethyl 7-cyano-3,4,5,6-tetrahydro-4-methylfuro[4,3,2-ef][3]benzazepine-2-carboxylate;
ethyl 7-chloro-9-dimethylamino-3,4,5,6-tetrahydro-4-methylfuro[4,3,2-ef][3]benzazepine-2-carboxylate;
ethyl 7-chloro-9-methylamino-3,4,5,6-tetrahydro-4-methylfuro[4,3,2-ef][3]benzazepine-2-carboxylate;
ethyl 7,9-dichloro-3,4,5,6-tetrahydro-4-methylfuro[4,3,2-ef][3]benzazepine-2-carboxylate; or
ethyl 7-dimethylamino-3,4,5,6-tetrahydro-4-methylfuro[4,3,2-ef][3]benzazepine-2-carboxylate;
or a pharmaceutically acceptable salt thereof.

8. A pharmaceutical composition comprising a compound of claim 1 and a suitable pharmaceutical carrier.

9. A pharmaceutical composition of claim 8 wherein the compound is 7-chloro-3,4,5,6-tetrahydro-2,4-dimethylfuro[4,3,2-ef][3]benzazepine.

10. A pharmaceutical composition of claim 8 wherein the compound is 2-bromo-7-chloro-3,4,5,6-tetrahydro-4-methylfuro[4,3,2-ef][3]benzazepine.

11. A pharmaceutical composition of claim 9 wherein the compound is:
ethyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-methanol;
7-chloro-3,4,5,6-tetrahydro-4-methylfuro[4,3,2-ef][3]benzazepine-2-carboxaldehyde;
methyl 7-chloro-3,4,5,6 tetrahydro-4-methylfuro[4,3,2-ef][3]benzazepine-2-carboxylate;
methyl 7-chloro-3,4,5,6-tetrahydro-4-methylfuro[4,3,2-ef][3]benzazepine-2-carboxylate;
2-propenyl-7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-carbonitrile;
7-chloro-3,4,5,6-tetrahydro-4-methylfuro[4,3,2-ef][3]benzazepine;
7-chloro-2-ethyl-3,4,5,6-tetrahydro-4-methylfuro[4,3,2-ef][3]benzazepine;
ethyl 7-chloro-3,4,5,6-tetrahydro-4-methylfuro[4,3,2-ef][3]benzazepine-2-propanoate;
7-chloro-3,4,5,6-tetrahydro-4-methylfuro[4,3,2-ef][3]benzazepine-2-propanol;
7-chloro-3,4,5,6-tetrahydro-4-methyl-2-[(2-propenyloxy)methyl]furo[4,3,2-ef][3]benzazepine;
7-chloro-3,4,5,6-tetrahydro-4-methyl-2-[(propyloxy)methyl]furo[4,3,2-ef][3]benzazepine;
7-chloro-3,4,5,6-tetrahydro-4-methyl-2-[(3-methyl-2-butenyloxy)methyl]furo[4,3,2-ef][3]benzazepine;
7-chloro-3,4,5,6-tetrahydro-4-methyl-2-[(2-propenylthio)methyl]furo[4,3,2-ef][3]benzazepine;
7-chloro-3,4,5,6-tetrahydro-4-methyl-2-(trifluoromethyl)furo[4,3,2-ef][3]benzazepine;
7-chloro-3,4,5,6-tetrahydro-4-methylfuro[4,3,2-ef][3]benzazepine-2-carboxamide;
N-butyl-7-chloro-3,4,5,6-tetrahydro-4-methylfuro[4,3,2-ef][3]benzazepine-2-carboxamide;
N,N-dimethyl-7-chloro-3,4,5,6-tetrahydro-4-methylfuro[4,3,2-ef][3]benzazepine-2-carboxamide;
7-chloro-3,4,5,6-tetrahydro-4-methyl-N-(phenylmethyl)furo[4,3,2-ef][3]benzazepine-2-carboxamide;
7-chloro-3,4,5,6-tetrahydro-4-methyl-N-(2-phenylethyl)furo[4,3,2-ef][3]benzazepine-2-carboxamide;
7-chloro-3,4,5,6-tetrahydro-N,4-dimethyl-N-(2-phenylethyl)furo[4,3,2-ef][3]benzazepine-2-carboxamide;
7-chloro-3,4,5,6-tetrahydro-4-methyl-N-(3-phenylpropyl)furo[4,3,2-ef][3]benzazepine-2-carboxamide;
phenylmethyl 7-chloro-3,4,5,6-tetrahydro-4-methylfuro[4,3,2-ef][3]benzazepine-2-propanoate;
2,7-dichloro-3,4,5,6-tetrahydro-4-methylfuro[4,3,2-ef][3]benzazepine;
7-chloro-2-[(4-chlorophenyl)methyloxy]-3,4,5,6-tetrahydro-4-methylfuro[4,3,2-ef][3]benzazepine;
7-fluoro-3,4,5,6-tetrahydro-4-methylfuro[4,3,2-ef][3]benzazepine-2-methanol;
7-chloro-9-dimethylamino-3,4,5,6-tetrahydro-4-methylfuro[4,3,2-ef][3]benzazepine-2-methanol;
7-bromo-3,4,5,6-tetrahydro-4-methylfuro[4,3,2-ef][3]benzazepine-2-methanol;
7-dimethylamino-3,4,5,6-tetrahydro-4-methylfuro[4,3,2-ef][3]benzazepine-2-methanol;
ethyl 7-cyano-3,4,5,6-tetrahydro-4-methylfuro[4,3,2-ef][3]benzazepine-2-carboxylate;
ethyl 7-chloro-9-dimethylamino-3,4,5,6-tetrahydro-4-methylfuro[4,3,2-ef][3]benzazepine-2-carboxylate;
ethyl 7-chloro-9-methylamino-3,4,5,6-tetrahydro-4-methylfuro[4,3,2-ef][3]benzazepine-2-carboxylate;
ethyl 7,9-dichloro-3,4,5,6-tetrahydro-4-methylfuro[4,3,2-ef][3]benzazepine-2-carboxylate; or
ethyl 7-dimethylamino-3,4,5,6-tetrahydro-4-methylfuro[4,3,2-ef][3]benzazepine-2-carboxylate.

12. A method of antagonizing α-adrenergic receptors in mammals that comprises administering to a subject in need thereof an effective amount of a compound of claim 1.

13. A method of claim 12 wherein the compound is 7-chloro-3,4,5,6-tetrahydro-2,4-dimethylfuro[4,3,2-ef][3]benzazepine.

14. A method of claim 12 wherein the compound is 2-bromo-7-chloro-3,4,5,6-tetrahydro-4-methylfuro[4,3,2-ef][3benzazepine.

15. A method of claim 12 wherein the compound is:
ethyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-methanol;
7-chloro-3,4,5,6-tetrahydro-4-methylfuro[4,3,2-ef][3]benzazepine-2-carboxaldehyde;
methyl 7-chloro-3,4,5,6-tetrahydro-4-methylfuro[4,3,2-ef][3]benzazepine-2-carboxylate;
2-propenyl 7-chloro-3,4,5,6-tetrahydro-4-methylfuro[4,3,2-ef][3]benzazepine-2-carboxylate;
7-chloro-3,4,5,6-tetrahydro-4-methylfuro[4,3,2-ef][3]benzazepine-2-carbonitrile;
7-chloro-3,4,5,6-tetrahydro-4-methylfuro[4,3,2-ef][3]benzazepine;
7-chloro-2-ethyl-3,4,5,6-tetrahydro-4-methylfuro[4,3,2-ef][3]benzazepine;
ethyl 7-chloro-3,4,5,6-tetrahydro-4-methylfuro[4,3,2-ef][3]benzazepine-2-propanoate;
7-chloro-3,4,5,6-tetrahydro-4-methylfuro[4,3,2-ef][3]benzazepine-2-propanol;
7-chloro-3,4,5,6-tetrahydro-4-methyl-2-[(2-propenyloxy)methyl]furo[4,3,2-ef][3]benzazepine;
7-chloro-3,4,5,6-tetrahydro-4-methyl-2-[(propyloxy)methyl]furo[4,3,2-ef][3]benzazepine;
7-chloro-3,4,5,6-tetrahydro-4-methyl-2-[(3-methyl-2-butenyloxy)methyl]furo[4,3,2-ef][3]benzazepine;
7-chloro-3,4,5,6-tetrahydro-4-methyl-2-[(2-propenylthio)methyl]furo[4,3,2-ef][3]benzazepine;
7-chloro-3,4,5,6-tetrahydro-4-methyl-2-(trifluoromethyl)furo[4,3,2-ef][3]benzazepine;
7-chloro-3,4,5,6-tetrahydro-4-methylfuro[4,3,2-ef][3]benzazepine-2-carboxamide;
N-butyl-7-chloro-3,4,5,6-tetrahydro-4-methylfuro[4,3,2-ef][3]benzazepine-2-carboxamide;
N,N-dimethyl-7-chloro-3,4,5,6-tetrahydro-4-methylfuro[4,3,2-ef][3]benzazepine-2-carboxamide;
7-chloro-3,4,5,6-tetrahydro-4-methyl-N-(phenylmethl)furo[4,3,2-ef][3]benzazepine-2-carboxamide;
7-chloro-3,4,5,6-tetrahydro-4-methyl-N-(2-phenylethyl)furo[4,3,2-ef][3]benzazepine-2-carboxamide;
7-chloro-3,4,5,6-tetrahydro-N,4-dimethyl-N-(2-phenylethyl)furo[4,3,2-ef][3]benzazepine-2-carboxamide;

7-chloro-3,4,5,6-tetrahydro-4-methyl-N-(3-phenylpropyl)furo[4,3,2-ef][3]benzazepine-2-carboxamide;

phenylmethyl 7-chloro-3,4,5,6-tetrahydro-4-methylfuro[4,3,2-ef][3]benzazepine-2-propanoate;

2,7-dichloro-3,4,5,6-tetrahydro-4-methylfuro[4,3,2-ef][3]benzazepine;

7-chloro-2-[(4-chlorophenyl)methyloxy]-3,4,5,6-tetrahydro-4-methylfuro[4,3,2-ef][3]benzazepine;

7-fluoro-3,4,5,6-tetrahydro-4-methylfuro[4,3,2-ef][3]benzazepine-2-methanol;

7-chloro-9-dimethylamino-3,4,5,6-tetrahydro-4-methylfuro[4,3,2-ef][3]benzazepine-2-methanol;

7-bromo-3,4,5,6-tetrahydro-4-methylfuro-[4,3,2-ef][3]benzazepine-2-methanol;

7-dimethylamino-3,4,5,6-tetrahydro-4-methylfuro[4,3,2-ef][3]benzazepine-2-methanol;

ethyl 7-cyano-3,4,5,6-tetrahydro-4-methylfuro[4,3,2-ef][3]benzazepine-2-carboxylate;

ethyl 7-chloro-9-dimethylamino-3,4,5,6-tetrahydro-4-methylfuro[4,3,2-ef][3]benzazepine-2-carboxylate;

ethyl 7-chloro-9-methylamino-3,4,5,6-tetrahydro-4-methylfuro[4,3,2-ef][3]benzazepine-2-carboxylate;

ethyl 7,9-dichloro-3,4,5,6-tetrahydro-4-methylfuro[4,3,2-ef][3]benzazepine-2-carboxylate; or ethyl 7-dimethylamino-3,4,5,6-tetrahydro-4-methylfuro[4,3,2-ef][3]benzazepine-2-carboxylate.

16. A method of reducing blood pressure in mammals that comprises administering to a subject in need thereof an effective amount of a compound of claim 1.

17. A method of treating peripheral vascular diseases in mammals that comprises administering to a subject in need thereof an effective amount of a compound of claim 1.

18. A method of treating benign prostatic hyperthrophy in mammals that comprises administering to a subject in need thereof an effective amount of a compound of claim 1.

19. A method of treating congestive heart failure in mammals that comprises administering to a subject in need thereof an effective amount of a compound of claim 1.

* * * * *

UNITED STATES PATENT AND TRADEMARK OFFICE
CERTIFICATE OF CORRECTION

PATENT NO. : 4,978,660

DATED : December 18, 1990

INVENTOR(S) : John J. Lafferty, Robert M. DeMarinis, Joseph W. Venslavsky

It is certified that error appears in the above-identified patent and that said Letters Patent is hereby corrected as shown below:

In Claim 2, column 37, line 10, replace "A compound represented by the formula:" with --- A compound of Claim 1 having the formula: ---.

Signed and Sealed this

Ninth Day of March, 1993

*Attest:*

STEPHEN G. KUNIN

*Attesting Officer*  *Acting Commissioner of Patents and Trademarks*